(12) United States Patent
Kirkin et al.

(10) Patent No.: US 7,723,107 B2
(45) Date of Patent: May 25, 2010

(54) PHARMACEUTICAL COMPOSITION FOR INDUCING AN IMMUNE RESPONSE IN A HUMAN OR ANIMAL

(75) Inventors: Alexei Kirkin, Copenhagen (DK); Karine Djandjougazian, Copenhagen (DK); Jesper Zeuthen, Hellerup (DK)

(73) Assignee: Dandrit Biotech A/S, Copenhagen O (DK)

( * ) Notice: Subject to any disclaimer, the term of this patent is extended or adjusted under 35 U.S.C. 154(b) by 36 days.

(21) Appl. No.: 12/182,089

(22) Filed: Jul. 29, 2008

(65) Prior Publication Data

US 2009/0029457 A1  Jan. 29, 2009

Related U.S. Application Data

(62) Division of application No. 10/495,511, filed as application No. PCT/DK2002/00802 on Nov. 29, 2002.

(60) Provisional application No. 60/336,706, filed on Dec. 7, 2001.

(30) Foreign Application Priority Data

Nov. 29, 2001  (DK)  ............................. 2001 01770

(51) Int. Cl.
*C12N 5/08* (2006.01)
(52) U.S. Cl. .................................... 435/366
(58) Field of Classification Search .................. None
See application file for complete search history.

(56) References Cited

FOREIGN PATENT DOCUMENTS

| WO | WO 01 41787 A1 | 6/2001 |
| WO | WO 01 82958 A2 | 11/2001 |
| WO | WO 01 82958 A3 | 11/2001 |
| WO | WO 02 072013 A2 | 9/2002 |
| WO | WO 02/072013 A3 | 9/2002 |

OTHER PUBLICATIONS

Geiger, James et al.; The Lancet, 2000, vol. 356, pp. 1163-1165.
Joshi et al., 2002, Clinc. Can. Res. vol. 8: 1948-1956.
Kawakami et al., 2001, Can. Res. vol. 61: 6194-6200.
Atanackovic et al., 2006, Canc. Biol. Ther. vol. 5: 1218-1225.
Nestle F O et al., Nature Medicine, United States Mar. 1998, vol. 4, No. 3, pp. 238-332.
Sandra et al., Journal of Immunotherapy, vol. 22, No. 1, Jan. 1999, pp. 16-24.
Shigeki et al., Japanese Journal of Cancer Research, vol. 87, No. 7, 1996, pp. 751-756.
Jäger et al., PNAS, vol. 97, No. 22, Oct. 24, 2000, pp. 12198-12203.
Thurner B et al., The Journal of Experimental Medicine, United States Dec. 6, 1999, vol. 190, No. 11, pp. 1669-1678.
Nishiyama, et al.; Clinical Cancer Research, vol. 7, Jan. 2001, pp. 23-31.
Kirkin et al., Cancer Immunol Immunother, vol. 41, pp. 71-81 (1995).
Chen et al., Cytogenet Cell Genet, vol. 79, pp. 237-240 (1997).
Li, et al., Clinical Cancer Research, vol. 2, pp. 1619-1625 (1996).
Alters et al., Journal of Immunotherapy, vol. 22(3), pp. 229-236 (1999).
Patard et al., Int. J. Cancer, vol. 64, pp. 60-64 (1995).
De Plean et al., Immunogenetics, vol. 40, pp. 360-369 (1994).
Brasseur et al., Int. J. Cancer, vol. 63, pp. 375-380 (1995).
Yamashita et al., Hepatology, vol. 24, No. 6, (1996).
Bartkova et al., Cancer Research, vol. 56, pp. 5475-5483 (1996).
Eura et al., Int. J. Cancer, vol. 64, pp. 304-308 (1995).
Boel et al., Immunity, vol. 2, pp. 167-175 (1995).
Brinkman, Genetics, vol. 95, pp. 10757-10762 (1998).
Brinkman et al., Cancer Research, vol. 59, pp. 1445-1448, (1999).
Chakraborthy et al., Cancer Immunol Immunother vol. 47, pp. 58-64 (1998).
Chambost et al., Blood, vol. 95, No. 11, (2000).
Chaux et al., J. Exp. Med., vol. 189, No. 5, pp. 767-777 (1999).
Chaux et al., Eur. J. Immunol., vol. 31, pp. 1910-1916 (2001).
Chen et al., The Journal of Biological Chemistry, vol. 273, No. 28, pp. 17618-17625 (1998).
Chen et al., Immunology, vol. 94, pp. 1914-1918, (1997).
Chen et al., Immunology, vol. 95, pp. 6919-6923, (1998).
Chomez et al., Cancer Research, vol. 61, pp. 5544-5551, (2001).
De Backer et al., Cancer Research 59, vol. 3157-3165, pp. 1999.
De Smet et al., Genetics, vol. 93, pp. 7194-7153 (1996).
Se Smet et al., Biochemical and Biophysical Research, vol. 241, pp. 653-657 (1997).
Van Der Bruggen et al., Science, vol. 254, pp. 1643-1647, (1991).
Van Den Eynde et al., J. Exp. Med., vol. 182, pp. 689-698 (1995).
Stevenson et al., Immunological Reviews, No. 145, pp. 228-250 (1995).
Visseren et al., Int. J. Cancer, vol. 73, pp. 125-130(1997).
Wang et al., The Journal of Immunology, vol. 161, pp. 3596-3606 (1998).
Weber et al., Cancer Research, vol. 54, pp. 1766-1771 (1994).
Yang et al., The Journal of Immunology, vol. 163, pp. 1737-1741 (1999).
Nestle et al., Nature Medicine, vol. 4, No. 3, pp. 328-332, (1998).
Thurner et al., Journal of Immunology Methods, vol. 223, pp. 1-15 (1999).
Jager et al., Immunology, vol. 97, No. 22, pp. 12198-12203, (2000).
Thurner et al., J. Exp. Med., vol. 190, No. 11, pp. 1669-1678, (1999).
Nishiyama et al., Clinical Cancer Research, vol. 7, pp. 23-31 (2001).
Shichijo, et al., "Induction of mage genes in lymphoid cells by the demethylating agent 5-aza-2'-deoxycytidine", (1996), Jpn J Cancer Res, vol. 87, pp. 751-756.

(Continued)

*Primary Examiner*—Amy E Juedes
(74) *Attorney, Agent, or Firm*—Birch, Stewart, Kolasch & Birch, LLP

(57) ABSTRACT

The present invention relates to a pharmaceutical composition for inducing an immune response in a human or animal, comprising dendritic cells loaded with at least five cancer/testis antigen and no lineage specific differentiation antigens or substantially no lineage specific differentiation antigens provided from at least one cancer cell line, as well as to isolated cell lines expressing a multiplicity of cancer testis antigens and no differentiation antigens, and to a method of inducing an immune response in a human or animal using the composition of the invention.

3 Claims, 10 Drawing Sheets

OTHER PUBLICATIONS

Coral, et al., "Prolonged upregulation of the expression of HLA class I antigens and costimulatory molecules on melanoma cells treated with 5-aza-2'-deoxycytidine (5-AZA-CdR)", (1999), J Immunotherapy, vol. 22, pp. 16-24.

Brinkman et al., Proc. Natl. Acad. Sci USA, vol. 95, pp. 10757-10762 (Sep. 1998).

Chen et al., The Journal of Biological Chemistry, vol. 273, No. 28, pp. 17618-17625 (1998).

Chen et al., Proc. Natl. Acad. Sci. USA, vol. 94, pp. 1914-1918 (Mar. 1997).

Chen et al., Proc. Natl. Acad. Sci. USA, vol. 95, pp. 6919-6923 (Jun. 1998).

De Smet et al., Proc. Natl. Acad. Sci. USA, vol. 93, pp. 7149-7153 (Jul. 1996).

De Smet et al., Molecular and Cellular Biology, vol. 19, No. 11, pp. 7327-7335 (Nov. 1999).

Duffour et al., Eur. J. Immunol., vol. 29, pp. 3329-3337 (1999).

Gaugler et al., J. Exp. Med., vol. 179, pp. 921-930 (Mar. 1994).

Herin et al., Int. J. Cancer, vol. 39, pp. 390-396 (1987).

Huang et al., The Journal of Immunology, vol. 162, pp. 6849-6854 (1999).

Jager et al., J. Exp. Med., vol. 191, No. 4, pp. 625-630 (Feb. 21, 2000).

Jurk et al., Int. J. Cancer, vol. 75, pp. 762-766 (1998).

Katano et al., Journal of Surgical Oncology, vol. 64, pp. 195-201 (1997).

Kirkin et al., Cancer Immunol Immunother, vol. 48, pp. 239-246 (1999).

Kugler et al., Nature Medicine, vol. 6, No. 3, pp. 332-336 (Mar. 2000).

Lethe et al., Int. J. Cancer, vol. 76, pp. 903-908 (1998).

Lucas et al., Cancer Research, vol. 58, pp. 743-752 (Feb. 15, 1998).

Lucas et al. Int. J. Cancer. vol. 87, pp. 55-60 (2000).

Manici et al., J. Exp. Med., vol. 189, No. 5, pp. 874-876 (Mar. 1, 1999).

Marovich et al., The Journal of Infectious Diseases, vol. 185, pp. 1242-1252 (2002).

Mulcahy et al., Int. J. Cancer, vol. 66, pp. 738-742 (1996).

Panelli et al., The Journal of Immunology, vol. 164, pp. 4382-4392 (2000).

Sahin et al., Proc. Natl. Acad. Sci. USA, vol. 92, pp. 11810-11813 (Dec. 1995).

Sallusto et al., J. Exp. Med., vol. 179, pp. 1109-1118 (Apr. 1994).

Sallusto et al., J. Exp. Med., vol. 182, pp. 389-400 (Aug. 1995).

Lurquin et al., Genomics, vol. 46, pp. 397-408 (1997).

Serrano, Int. J. Cancer, vol. 83, pp. 664-669 (1999).

Tanzarella, Cancer Research, vol. 59, pp. 2668-2674 (Jun. 1, 1999).

Tuyaerts et al., Journal of Immunological Methods, vol. 264, pp. 135-151 (2002).

Van Pel et al., Immunological Reviews, No. 145, pp. 229-250 (1995).

Figure 3
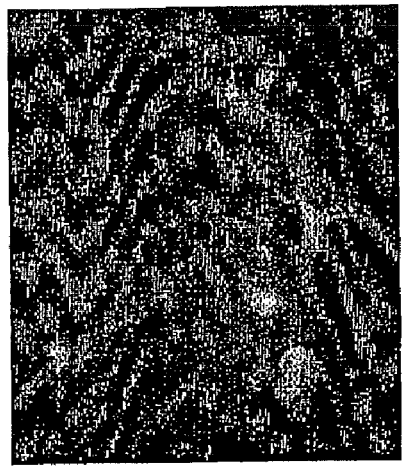
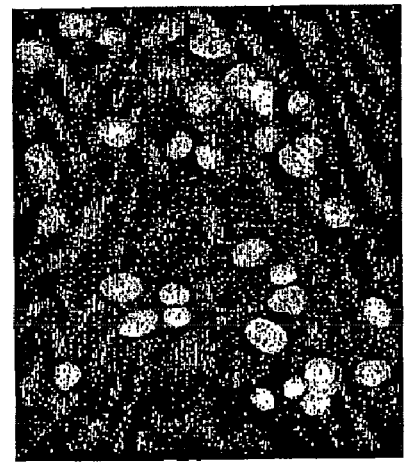
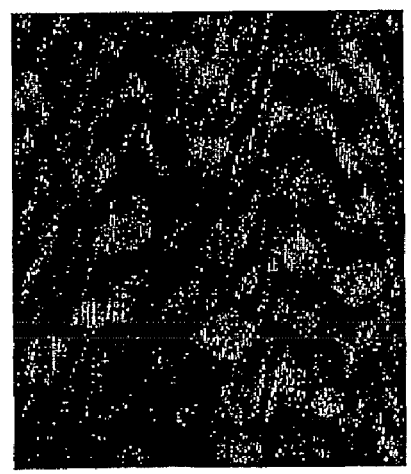
gp100
DAPI
DDM-1.29
DDM-1.7

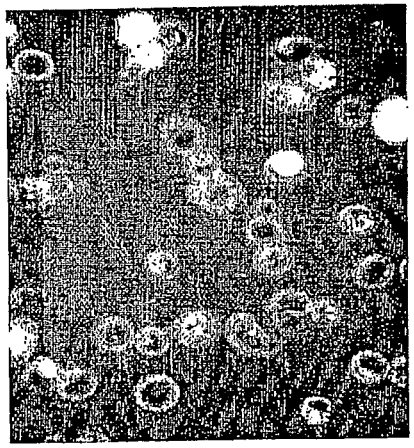
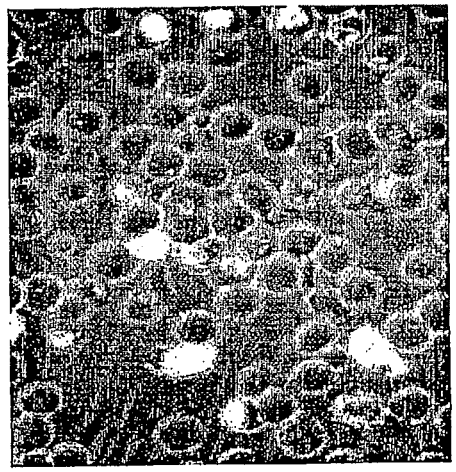
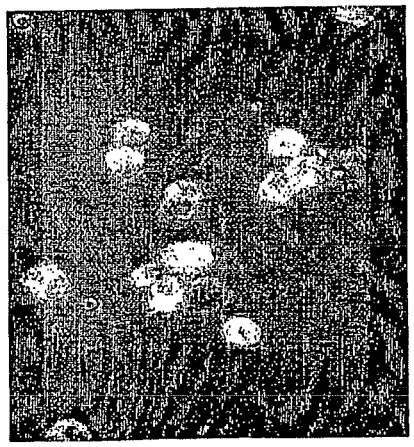
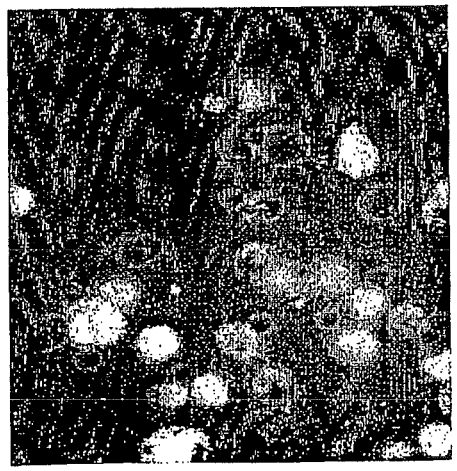
Figure 6

PHARMACEUTICAL COMPOSITION FOR INDUCING AN IMMUNE RESPONSE IN A HUMAN OR ANIMAL

This Application is a Divisional Application of U.S application Ser. No. 10/495,511 which is the National Stage under 35 U.S.C. §371 of International Application No. PCT/DK2002/00802 which has an International filing date of Nov. 29, 2002, which claims priority to U.S. Provisional Application No. 60/336,706 filed on Dec. 7, 2001, and claiming priority to Denmark Application PA 2001 01770 filed on Nov. 29, 2001, The entire contents of all applications listed above are hereby incorporated by reference.

TECHNICAL FIELD

The present invention relates to a pharmaceutical composition for inducing an immune response in a human or animal. In another aspect the invention relates to a method for obtaining autologous dendritic cells loaded with at least five cancer/testis antigen and no lineage-specific differentiation antigen or substantially no lineage-specific differentiation antigen. In another aspect the present invention relates to an isolated melanoma cell line. In a further aspect the present invention relates to a use of the composition as an immunotherapeutic vaccine and a use of autologous dendritic cells as antigen presenting cells in a pharmaceutical composition or a vaccine. In an even further aspect the present invention relates to a method for inducing an immune response in a human or animal.

BACKGROUND ART

Advanced cancers represent one of the major causes of human death. No effective methods of treatment have been suggested so far. Cancer immunotherapy aims at destroying tumor cells by immunological mechanisms. Immunotherapy compared to conventional methods of cancer therapy like surgery, radiation, and chemotherapy, is much less toxic, and no serious complications have been described so far. In addition, immunotherapy has the potency to work at different stages of disease. At initial stages it could be a good supplementary treatment to surgical removal of primary tumors, aiming to prevent development of disseminated disease. At advanced stages of disease it could be the only means of treatment, as conventional methods are often ineffective.

The main function of the immune system is to identify and destroy foreign substances (antigens) that invade the organism. The immune system is able to discriminate "self" from "non-self", and under normal conditions only to develop an immune response against foreign or "non-self" antigens. Even though cancer cells originate from the organisms own cells they are treated as foreign by the natural immune system. However, this natural immune response is not strong enough in order to block the appearance and growth of the tumor. The task of immunotherapy is to increase the ability of the immune system to recognize tumor cells and to develop effective mechanisms of tumor elimination. The two main questions in any specific immunotherapy are which antigens to target and to find the optimal antigen presentation to the immune system.

Tumor associated antigens (TAA) recognized by cytotoxic T lymphocytes (CTL) is the most efficient component to be targeted among known effector mechanisms in anti-tumor immunity. There are two major types of TAA: unique antigens, present only in very few tumors and therefore not useful as general targets, and shared or common TAA, present in many tumors. Three major groups of shared antigens are currently considered as potential targets for immunotherapy and have all been shown to induce generation of cytotoxic T lymphocytes. The three groups are: Cancer/testis antigens (CT antigens), Tumor over-expressed antigens, and Lineage-specific differentiation antigens.

CT antigens are encoded by cancer or germ line specific genes, representing one of the largest groups of shared tumor-associated antigens. CT antigens were originally discovered in melanomas but have also been found in many other human malignancies. Among normal tissue they are only expressed in testis and in some cases in placenta. Normal cells expressing these antigens lack expression of MHC molecules and therefore these antigens are normally not accessible for recognition by T lymphocytes.

This makes CT antigens very attractive targets for specific cancer immunotherapy. Recent clinical trials have demonstrated tumor regression in a significant number of melanomas and bladder cancer patients by targeting of one specific CT antigen ((Nishiyama et al 2001, Clin. Cancer Res., v. 7, pp. 23-31; Thurner et al., 1999, J. Exp. Med., v. 190, pp. 1669-1678)). CT antigen recognition by T cells has only been reported for some CT antigens and the corresponding peptide epitopes determined. However, all CT antigens could be considered potential targets for immunotherapy. A correlation of the expression of MAGE-A antigens and tumor progression has been found in a number of malignancies ((Brasseur et al., 1995, Int. J. Cancer, v. 63, pp. 375-380; Eura et al., 1995, Int. J. Cancer, v. 64, pp. 304-308; Katano et al., 1997, J. Surg. Oncol., v. 64, pp. 195-201; Patard et al., 1995, Int. J. Cancer, v. 64, pp. 60-64)). Another group of CT antigens, the MAGE-B antigens, shows a significantly lower tumor-specific expression than the MAGE-A antigens. A third group, the MAGE-C antigens, displays an expression pattern that resembles the pattern of the MAGE-A antigens. No CTL response against MAGE-C antigens has been reported yet.

Several non-MAGE proteins with the characteristics of CT antigens have been described. One of them, NY-ESO-1 is one of the most immunogenic tumor antigens identified to date. Clinical trials with peptide immunization of melanoma patients demonstrated stabilization of disease and regression of some metastases in some patients ((Jäger et al., 2000, Proc. Natl. Acad. Sci. U.S.A, v. 97, pp. 12198-12203)).

In contrast to CT antigens, tumor over-expressed antigens lack strictly tumor specific expression, as their expression could be detected in low levels in some normal tissue types other than testis. Development of immunotherapy to some of these antigens could be beneficial for cancer patients, and presently such antigens like CEA, p53, HER-2/Neu, MUC-1 and alpha-fetoprotein are being intensively investigated as possible targets in clinical trials. The group of tumor over-expressed antigens has only recently been used as targets in clinical trials, and thus data on the efficiency of induction of therapeutic immune responses are absent.

The lineage specific antigens, melanocyte differentiation antigens and prostate-associated antigens, have so far only been described for two types of human cancers: melanomas and prostate cancer. This group of antigens is expressed both in normal differentiated tissue and in two types of human cancers. In normal differentiated tissue these antigens very rarely induce an immune response, however, these proteins become immunogenic in cancer cells, and in the case of melanomas, it is possible to detect T-killer cells reactive against melanocyte differentiation antigens. A prevailing number of clinical trails directed against melanomas or prostate cancer employ targeting of differentiation antigens.

Among the groups of tumor associated antigens the most promising data using TAA as targets for immunotherapy were obtained with some of the MAGE proteins. However, especially in case of melanomas, the therapeutic effect was unstable, and some metastases continued to grow. These metastases were usually negative for expression of the MAGE antigens used for immunization ((Thurner et al., 1999, J. Exp. Med., v. 190, pp. 1669-1678)).

One possibility for inducing a polyvalent immune response is to employ whole tumor cells or material derived from whole cells. WO 9003183, U.S. Pat. Nos. 5,840,317, and 6,187,306 describes several melanoma cell based vaccine preparations. U.S. Pat. No. 4,108,983 discloses a first generation melanoma vaccine derived from melanoma cells lysed by a vaccinia virus.

U.S. Pat. Nos. 5,635,188 and 5,030,621 disclose a vaccine of cell surface antigens from melanoma cells that are shed into the culture medium and subsequently used as an antimelanoma vaccine. Similarly, U.S. Pat. No. 5,484,596 discloses a method of cancer therapy wherein irradiated tumor cells are injected into a human patient as a vaccine. U.S. Pat. No. 6,187,306 relates to melanoma cell lines expressing shared immunodominant melanoma antigens and methods of use.

An important aspect of any vaccine therapy is the way of vaccine administration. In recent years it has been realized that the most efficient way of antigen delivery to T cells, especially to naïve T cells, is by way of dendritic cells. Dendritic cells (DC) are the most efficient antigen presenting cells and DC based immunotherapy have already been used in different settings for treatment of cancer ((Kugler et al., 2000, Nat. Med., v. 6, pp. 332-336; Nestle et al., 1998, Nature (Med.), v. 4, pp. 328-332; Thurner et al., 1999, J. Exp. Med., v. 190, pp. 1669-1678)) demonstrating high potency of this way of immunization.

One of the unique properties of DC is their ability to uptake exogenous proteins by endocytosis, which are then processed and presented as peptide epitopes on their surface in conjunction with MHC class I antigens. The antigen presenting dendritic cells can be recognized by cytotoxic T cells. This property is extremely important when tumor cell antigens are applied in form of tumor lysates or apoptotic bodies added exogenously. High endocytic activity is believed to be associated with the immature state of DC differentiation based on comparison of immature and mature DC ((Sallusto et al., 1995, J. Exp. Med., v. 182, pp. 389-400)). The possibility that differences in the endocytic activity among immature DC could exist has never been considered.

WO 0127245 discloses a method of obtaining dendritic precursor cells from peripheral blood by standard leukapheresis, buoyant density gradient centrifugation and culture of the cells ex vivo in serum free medium for 40 hours in the absence of exogenously added cytokines.

WO 0146389 relates to a method for generating dendritic cells from leukapheresis products in closed systems, by using culture medium devoid of non-human proteins. Clinical grade cytokines (IL-4 and GM-CSF) are used in the culture medium and TAA are added for loading of the DC's.

Thurner et al., 1999, J. of Immunological Methods 223: 1-15, relates to a method for reproducible generation of large numbers of mature DC's from CD14+ monocytes by a two step method where cytokines are added after day 1.

The combination of dendritic cells with TAA's is also disclosed in WO 0128583, which relates to an immunotherapeutic vaccine providing antigen presenting cells mat have been pulsed with a disrupted cell preparation which includes cell membranes of cancer cells infected with recombinant vaccinia virus encoding at least one immunostimulating molecule. Also included is autologous DC's that presents a mixture of antigens from melanoma cell lines infected with a recombinant vaccinia virus encoding IL-2. In WO 0129192 a method is disclosed for inducing a tumor specific immune response in a patient, wherein antigen presenting cells from the patient are incubated with dead cell portions possessing at least one tumor antigen and the resulting loaded antigen presenting cells are administered to the patient.

Although the immunotherapeutic vaccines for treatment of cancer have improved over the recent years a need still exists for safer and more efficient compositions for use in cancer immunotherapy. Such vaccines should be polyvalent targeting several CT antigens to avoid outgrowth of antigen loss variants. They should be safer without the potential risk of targeting antigens expressed in normal tissue. They should be optimized for the presentation and delivery of the antigens to the T cells and also care should be taken to select the most efficient TAA's as targets.

DISCLOSURE OF INVENTION

The present invention has solved these problems by careful selection of the melanoma cell lines to supply the most effective TAA's followed by a subsequent screening in order to avoid any antigens which potentially could be harmful to the patient. Also the antigen presenting cells have been optimized for their endocytic activity before loading the DC's with the whole melanoma cell lysate.

In a first aspect the present invention relates to a pharmaceutical composition for inducing an immune response in a human or animal, comprising dendritic cells presenting a multiplicity of cancer/testis antigens, wherein a) at least five cancer/testis antigens and no lineage specific differentiation antigens or substantially no lineage specific differentiation antigens are presented by the dendritic cells, b) the cancer/testis antigens are provided from at least one cancer cell line expressing at least five different cancer/testis antigens and no lineage specific differentiation antigens or substantially no lineage specific differentiation antigens, and c) the dendritic cells are immature (CD1a positive, CD14 negative, and CD83 negative) during loading of the cancer/testis antigens.

In a second aspect the present invention relates to a method for obtaining human or animal autologous dendritic cells loaded with at least five cancer/testis antigens and no lineage specific differentiation antigens or substantially no lineage specific differentiation antigens, comprising the steps:

a) providing at least one cancer cell line expressing the at least five cancer/testis antigens and no lineage specific differentiation antigens or substantially no lineage specific differentiation antigens, b) providing autologous dendritic cells from said human or animal, c) using a seeding density of monocytes between $5 \times 10^6$-$20 \times 10^6$ cells per 25 cm$^2$, d) culturing said dendritic cells ex vivo in growth medium without any cytokines in an initial growth phase, followed by a second growth phase in medium comprising cytokines, and e) loading said dendritic cells from d) with the cancer/testis antigens obtained from a whole cell lysate of the at least one cancer cell line from a).

In a third aspect the present invention relates to an isolated melanoma cell line, expressing at least five cancer/testis antigens and no melanocyte differentiation antigens or substantially no melanocyte differentiation antigens.

In a fourth aspect the present invention relates to a use of a multiplicity of cancer/testis antigens obtainable from an isolated cancer cell line of claim 28 in a pharmaceutical composition or vaccine formulation.

In a fifth aspect the present invention relates to a use of dendritic cells as antigen presenting cells in a pharmaceutical composition or a vaccine, and where the said dendritic cells are loaded with the antigens in their immature state at which point the dendritic cells are CD1a positive, CD14 negative, CD83 negative, wherein the dendritic cells have been cultured ex vivo in growth medium without any cytokines in an initial growth phase, followed by a second growth phase in medium comprising cytokines before loading the dendritic cell with at least five cancer/testis antigen.

In a sixth aspect the present invention relates to a method for inducing an immune response in a human or animal comprising the steps:
a) providing at least one cancer cell line expressing at least five cancer/testis antigens and no lineage specific differentiation antigens or substantially no lineage specific differentiation antigens,
b) providing autologous dendritic cells from said human or animal,
c) culturing said dendritic cells ex vivo in growth medium without any cytokines in an initial growth phase, followed by a second growth phase in medium comprising cytokines,
d) loading said dendritic cells from c) with the cancer/testis antigens obtained from a whole cell lysate of the at least one cancer cell line from a), and
e) administering said loaded dendritic cells from d) to said human or animal.

BRIEF DESCRIPTION OF THE DRAWING(S)

The invention is explained in detail below with reference to the drawing(s), in which FIG. 1 shows sensitivity to lysis by gp100 and MART-1/Melan A-specific cytotoxic T lymphocyte (CTL) clones of a number of DDM-1 melanoma clones.

FIG. 3 shows expression of melanocyte differentiation antigen gp100 in DDM-1.7 and DDM-1.29, cells determined by immunostaining.

FIG. 6 shows uptake by endocytosis of fluorospheres by four cultures of immature dendritic cells.

BEST MODE(S) FOR CARRYING OUT THE INVENTION

Figure 1:
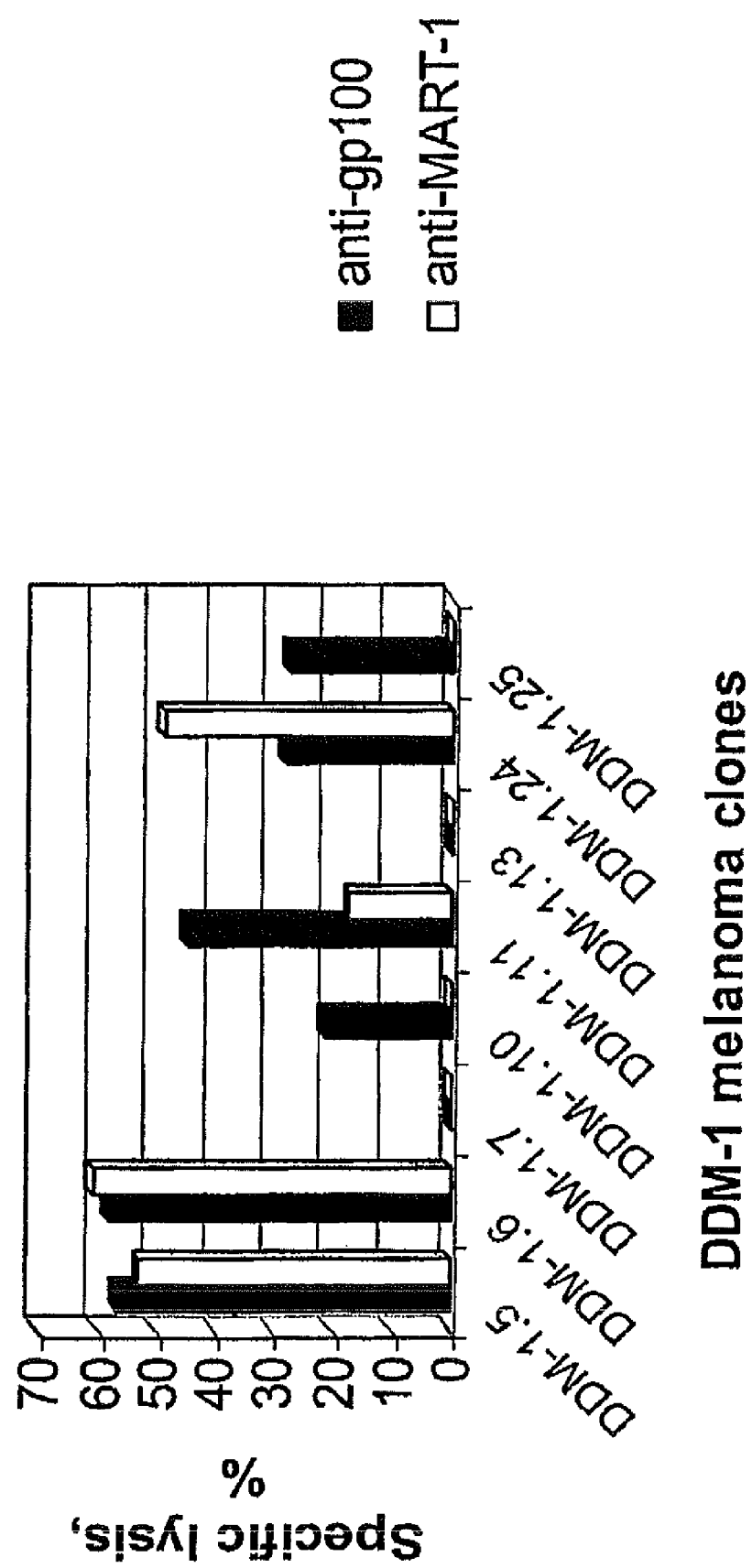

Prior to a discussion of the detailed embodiments of the invention, a definition of specific terms related to the main aspects of the invention is provided.

DEFINITIONS

Cytotoxic T-lymphocytes: Lymphocytes are small mononuclear white blood cells present in lymphoid tissues and circulating blood and lymph. There are two main functional types, B-lymphocytes and T-lymphocytes, which take part in antigen specific immune reactions. T-lymphocytes (T cells) are a type of small antigen-specific lymphocyte originating in thymus (in mammals) and present in secondary lymphoid tissues (e.g. lymph nodes, spleen) and blood, and which are involved in cellular immune reactions and aiding the production of antibodies. T lymphocytes bear antigen-specific receptors on their surface and only react to foreign antigen presented to them on the surface of a cell. The main types of T lymphocytes are: cytotoxic T cells which recognize and kill body cells mat have become antigenically altered in some way (e.g. by virus infection), helper T cells which are activated by foreign antigen on the surface of antigen-presenting cells and in turn activate the appropriate B cells, suppressor T cells which are involved in suppressing immune responses and the general regulation of the immune system.

Cancer/testis antigens (CT-antigens): Antigens encoded by cancer or germ line specific genes, representing one of the largest groups of shared tumor-associated antigens. CT-antigens were originally discovered in melanomas but have also been found in many other human malignancies. Among normal tissue they are only expressed in testis and in some cases in placenta. Normal cells expressing these antigens lack expression of MHC molecules and therefore these antigens are normally not accessible for recognition by T lymphocytes.

Lineage specific differentiation antigens: A group of differentiation antigens, so far only described for melanomas and prostate cancer. These antigens are only immunogenic in cancer cells and the group comprises the melanocyte differentiation antigens gp100, Melan-A/MART-1, Tyrosinase, TRP-1, TRP-2, MC1R, AIM-1 and the prostate-associated antigens PSA (prostate specific antigen), PSMA (prostate specific membrane antigen), PAP (prostate associated phosphatase), and PSCA (prostate stem cell antigen).

Melanocyte differentiation antigens: A group of antigens expressed both in normal differentiated melanocytes and in melanomas. In normal differentiated melanocytes these antigens very rarely induce an immune response, however, these proteins become immunogenic in cancer cells, and in the case of melanomas, it is possible to detect T-killer cells reactive against melanocyte differentiation antigens. The proteins are thought to be responsible for the synthesis of the pigment melanin.

Dendritic cells: Type of non-lymphocyte cell in some lymphoid tissues, which acts as an antigen-presenting cell by endocytosis of exogeneous proteins which are then processed and presented as epitopes on their surface in conjunction with MHC class I and II antigens. The antigen presenting dendritic cells can be recognized by cytotoxic T cells and T-helper cells. The maturation state of the dendritic cells are important for their phagocytic/endocytic activity. Immature dendritic cells are the most efficient cells for loading antigens.

Immature dendritic cells: Dendritic cells in which the expression of certain cell markers CD1a, CD14 and CD83 is characterized by a high expression of CD1a (more than 50% of DC's in the population are positive for CD1a), no expression or low expression of CD14 (less than 15% of DC's in the population are positive for CD14) and low expression of CD83 (less than 25% of DC's in the population are positive for CD83).

Exosomes: Exosomes are membrane vesicles of 30 to 100 nm in diameter, of endocytic origin, and are produced and secreted in vitro by living cells of diverse origin.

Cytokines: Immune system proteins that are biological response modifiers. They coordinate antibody and T-cell immune system interactions, and amplify immune reactivity. Cytokines include monokines synthesised by macrophages and lymphokines produced by activated T lymphocytes and natural killer cells. Monokines include interleukin (IL)-1, tumor necrosis factor (TNF), α- and β-interferon (IFN), and colony-stimulating factors. Lymphokines include IL's, γ-IFN, granulocyte-macrophage colony-stimulating factor (GM-CSF), and lymphotoxin. Endothelial cells and fibroblasts and selected other cell types may also synthesise cytokines. Examples of suitable cytokines according to the invention include IL-4, GM-CSF, IL-13, IFN-γ, Flt-31, SCF, TNF-α

Melanoma: A malignant cancer or tumor of varying degree of severity, which tend to spread or metastasize in advanced stages of the disease.

Loading dendritic cells: The uptake of exogeneous proteins by endocytosis and the presentation of peptide epitopes on the surface of the dendritic cell. Sometimes also referred to as "pulsing".

The term "substantially no lineage specific/melanocyte differentiation antigens" in connection with the present invention means that the cancer/melanoma cell line to be used for preparing a whole cell lysate should not express lineage specific/melanocyte differentiation antigens in amounts that will result in stimulation of an immune response against the lineage specific/melanocyte differentiation antigen. In practice, this means that cancer/melanoma cells are insensitive to lysis by cytotoxic T lymphocytes specific against lineage specific/melanocyte differentiation antigens (lysis is less than 10%, particularly less than 5%, and more particularly less than 2% in a 4-hours cytotoxicity test), and only 1-2% of cells are positively stained by antibodies against lineage specific/melanocyte differentiation antigens. In addition, the amount of RNA transcripts from the genes encoding the lineage specific/melanocyte differentiation antigens is at least about 100 fold lower in these cell lines as compared to highly sensitive cell lines, as determined by semi-quantitative RT-PCR.

Immune response: A selective response mounted by the immune system of vertebrates in which specific antibodies and/or cytotoxic cells are produced against invading microorganisms, parasites, transplanted tissue and many other substances which are recognized as foreign by the body (antigens). The production of antibodies circulating in the blood is known as a humoral immune response, the production of cytotoxic cells as a cell-mediated or cellular immune response.

Immunotherapeutic vaccine: A vaccine administered to treat and/or prevent further progression of a disease in a host already diagnosed with the disease.

Autologous cells: Cells that are an individual's own cells.

Allogeneic: Genetically different, but of the same species.

Antigen presenting cell: Specialized lymphoid cell such as dendritic cells, B cells and monocytic cells, which are capable of inducing T cell activation.

Monocyte: Phagocytic white blood cell related to macrophages. Monocytes represent another type of antigen presenting cells, which mainly re-activate previously sensitized cytotoxic T lymphocytes.

Precursor dendritic cells: CD14+ monocytes present in peripheral blood or CD34+cells present in bone marrow or in peripheral blood (especially after mobilization).

Immunodominant: Antigen present in mixture with other antigens predominantly stimulates immune response against itself.

The present invention relates to an improved therapeutic composition to be used as e.g. an immunotherapeutic vaccine. The most efficient way of antigen delivery to T cells, especially to naïve T cells, is by way of autologous dendritic cells. Several different tumor associated antigens from either of the three groups: CT antigens, tumor over-expressed antigens, and lineage specific antigens have been used in clinical trials and so far the most promising results have been seen with antigens from the group of cancer/testis antigens.

Tumor over-expressed antigens, in contrast to CT antigens, lack strictly tumor specific expression, as their expression could be detected in some normal tissues other than testis, albeit at significantly lower levels than in tumor cells. Such distribution prevents the development of strong tumor rejection immunity (due to elimination of highly reactive T lymphocytes in the course of tolerance induction) and in case a response could be generated, the potential risk of developing autoimmunity will be high. The group comprises a large number of antigens and several have recently been targets in clinical trials.

The same restrictions as mentioned above also apply to the lineage specific antigens, which group includes the differentiation antigens. This group of antigens is also expressed in corresponding normal differentiated tissue, and in healthy individuals they are very seldom inducing immune attack due to the tolerance to "self" proteins. For unknown reasons, these normal proteins become immunogenic in cancer cells, and in case of melanomas, T-killer cells reactive against melanocyte differentiation antigens could easily be detected in patients, but not in healthy individuals. A prevailing number of clinical trails directed against melanomas or prostate cancer employ targeting of differentiation antigens.

It is an object of the present invention to specifically avoid the presence of over-expressed and lineage-specific differentiation antigens in antigen mixture used for immunization. In the case of melanomas cell lines, the group of over-expressed antigens, are extremely seldom able to induce an immune response, therefore excluding a need for negative selection for this group of antigens. Regarding melanocyte differentiation antigens they should not be present, but if present the amount should not be sufficient to result in stimulation of an immune response against them (in practice this means that the amount of RNA transcripts from the genes encoding the melanocyte differentiation antigens is at least about 100 fold lower in the cell lines of the invention as compared to highly sensitive cell lines, as determined by semi-quantitative RT-PCR). The presence of such immunodominant proteins should be avoided and particularly the proteins gp100, Melan A/MART-1 and tyrosinase should not be present.

It is also an object of the present invention to provide cell lines expressing at least three, particularly at least five CT antigen and more particularly as many CT antigens as possible, which should be immunodominant. Surprisingly such cell lines could be provided from melanoma patients, which after removal of the stage III or stage IV tumor have had a long disease-free period (more than five years), indicative of immunogenicity of the tumor cells in vivo. Individual subclones from such cell lines should subsequently be screened for the absence of any melanocyte differentiation antigens, particularly gp100, Melan A/MART-1 and tyrosinase.

In addition to melanoma immunotherapy the present invention also provides a method for inducing an immune response in a human or animal for other types of cancer. The requirements are that the antigens targeted are shared antigens and present in other types of malignancies, predominantly in solid tumors. Particularly these types of cancer may comprise colorectal carcinoma, pancreatic cancer, breast cancer, ovarian cancer, prostate cancer, squamous cell carcinoma, sweat gland carcinoma, renal cell carcinoma, hepatoma, cervical cancer, lung carcinoma, small cell lung carcinoma or bladder carcinoma.

In one embodiment the present invention therefore relates to a pharmaceutical composition for inducing an immune response in a human or animal, comprising dendritic cells presenting a multiplicity of cancer/testis antigens, wherein
a) at least five cancer/testis antigens and no lineage specific differentiation antigens or substantially no lineage specific differentiation antigens are presented by the dendritic cells,
b) the cancer/testis antigens are provided from at least one cancer cell line expressing at least five different cancer/testis antigens and no lineage specific differentiation antigens or substantially no lineage specific differentiation antigens, and
c) the dendritic cells are immature (CD1a positive, CD14 negative, and CD83 negative) during loading of the cancer/testis antigens.

Advantageously the loaded dendritic cells may subsequently be matured by the addition of maturation factors.

Dendritic cells are the most efficient antigen presenting cells as discussed above, and it is another objective of the present invention to provide dendritic cells and particularly autologous dendritic cells generated from CD14+ monocytes isolated from peripheral blood or CD34+ cells from peripheral blood or bone marrow, which have been optimized with respect to their endocytic/phagocytic activity and CD1a expression. This activity is believed to relate to dendritic cells in their immature state. In order to obtain such activated cells most reports have employed the "GM-CSF+IL-4 method" by Sallusto and Lanzavecchia, (1994, J. Exp. Med. 179: 1109). Other suitable cytokines include IL-4, GM-CSF, IL-13, IFN-γ, Flt-31, SCF, TNF-α(Alters et al., 1999, J. Immunother., v. 22, pp. 229-236), in particular in relation to the present invention the cytokines are selected from GM-CSF and IL-4.

Surprisingly we have now found, as shown in Example 2 below, that this method can be further optimized and that culture ex vivo in growth medium without any cytokines in an initial growth phase, followed by a second growth phase in fresh medium comprising cytokines before loading the dendritic cells results in DC's with increased endocytic activity. The initial growth phase according to the present invention is from 6-48 hours, particularly from 12-34 hours, and more particularly from 20-28 hours.

Previously it was believed that the endocytic activity of all immature dendritic cells was equally good irrespective of the culture method. Now we have discovered that by applying a reported method for the production of stable mature dendritic cells and loading the dendritic cells in their immature state before addition of maturation factors, it is possible to obtain immature dendritic cells, which have been optimized in respect of their endocytic activity.

In another embodiment the present invention therefore relates to a pharmaceutical composition as stated above, wherein the dendritic cells have been cultured ex vivo in growth medium without any cytokines in an initial growth phase, followed by a second growth phase in medium comprising cytokines before loading the dendritic cells with at least one cancer/testis antigen.

Since a multiplicity of CT-antigens should be provided and particularly more than five CT-antigens, the present invention in a further embodiment relates to a pharmaceutical composition as described above, wherein the at least five cancer/testis antigen are provided from a whole cell lysate of the at least one cancer cell line expressing no lineage specific differentiation antigens or substantially no lineage specific differentiation antigens. A whole cell lysate can be obtained in several ways from cells, like e.g. tumor cells or other cell types, by disrupting the cells, e.g. by several cycles of freezing and thawing. In the cell lysate, which comprises the soluble material, normally particles are removed by centrifugation and/or filtration.

In one particular embodiment the present invention relates to a pharmaceutical composition as described above wherein the cancer cell line is a melanoma cell line, and the lineage specific differentiation antigens are melanocyte differentiation antigens.

In a further embodiment the melanocyte differentiation antigens comprise gp100, Melan A/Mart-1, and tyrosinase.

Dendritic cells cultured ex vivo according to the present invention will be optimized in respect of their endocytic activity and CD1a expression, and they can advantageously be applied for antigen presentation in any composition or vaccine for use in immunotherapy. Accordingly in a further embodiment the present invention relates to a use of autologous dendritic cells as antigen presenting cells in a pharmaceutical composition or a vaccine, wherein said autologous dendritic cells have been cultured ex vivo in growth medium without any cytokines in an initial growth phase, followed by a second growth phase in medium comprising cytokines before loading the dendritic cell in their immature state with at least five cancer/testis antigen.

Other ways of obtaining dendritic cells presenting the antigens according to the invention, e.g. by whole cell fusion, would also be possible. This could be accomplished by fusion of dendritic cells with the cells lines according to the invention.

In a further embodiment antigen presentation is performed by the use of exosomes. Exosomes are small membrane vesicles of endocytic origin that are secreted by most cells in culture and have recently been described in antigen-presenting cells and they are capable of stimulating immune responses in vivo (Théry et al., 2002, Nature Reviews Immunology 2:569-579).

In a still further embodiment the present invention relates to a method for obtaining autologous dendritic cells loaded with at least five cancer/testis antigen and no lineage specific differentiation antigens or substantially no lineage specific differentiation antigens, comprising the steps:
a) providing at least one cancer cell line expressing at least five cancer/testis antigens and no lineage specific differentiation antigens or substantially no lineage specific differentiation antigens,
b) providing autologous dendritic cells from said human or animal,
c) culturing said dendritic cells ex vivo in growth medium without any cytokines in an initial growth phase, followed by a second growth phase in medium comprising cytokines, d) loading said dendritic cells from c) with the cancer/testis antigens obtained from a whole cell lysate of the at least one cancer cell line from a).

Advantageously the dendritic cells may subsequently be matured after step d) by the addition of maturation factors such as e.g. IL-1β, IL-6, TNF-α; and PGE2.

In another embodiment the present invention relates to a pharmaceutical composition obtainable by performing the steps a) through d) above, followed by a maturation step.

Employing the known methods for the generation of dendritic cells from populations of mononuclear cells good yields of dendritic cells have been difficult to obtain. The average yield of dendritic cells from a starting population of mononuclear cells has previously been reported to be about 5% (Marovitch et al., 2002, J. Infect. Dis. 186: 1242-1252). In order to get $50 \times 10^6$ dendritic cells, which is required for one complete cycle of vaccination, it is necessary to start with $10^9$ mononuclear cells.

Assuming that the cell concentration during adsorption is usually $5 \times 10^6$/ml, this amount of cells will require 0,2 l of medium for the adsorption step, and the same amount of medium for further cell cultivation. About 60 μg of GM-CSF and 30 μg of IL-4 will be required for the generation of dendritic cells, as well as large amount of tissue culture plastic ware. This will result in a net price per vaccine which will be rather high. In addition, in order to isolate $10^9$ mononuclear cells from the blood, up to 1 L of blood will be required, which is hardly possible to draw from a patient even if performed in two drawings separated significantly in time considering the poor health of the patient.

One possibility is to employ leukapheresis that permits the isolation of significant number of mononuclear cells. This procedure is often used to produce a large number of dendritic cells (see e.g. Thurner et al. 1999, J. Immunol. Methods 223: 1-15). The procedure of leukopheresis is, however, highly time-consuming and costly, which in turn will increase the total price of vaccine production. In addition, only one patient can be processed on a single leukapheresis equipment. This will limit the productive capacity of manufacturing procedures.

Alternatively, the efficiency of the generation of dendritic cells from monocytes could be increased. For example Tuyaerts et al. 2002, (J. Immunol. Methods 264: 135-151) have reported the adaptation of the method of dendritic cell production for Nunc Cell Factories, and reported a yield of dendritic cells up to 40% of the starting number of monocytes (or 13% of the starting number of mononuclear cells, as monocytes represent on average one third of the mononuclear cells). The generated dendritic cells, however, were lacking the expression of the CD1a marker, which may indicate their incomplete differentiation. Since expression of CD1a is essential for the purpose of the present invention this method cannot be employed for our purpose.

Therefore, we have instead optimized the procedure for generation of immature dendritic cells from blood monocytes, closely monitoring the increasing efficiency of the monocyte transformation into dendritic cells, as well as the generation of fully competent immature dendritic cells. As a read out system for the generation of competent immature dendritic cells, we have selected following criteria: high (more than 50%) expression of CD1a marker, no or low (less than 15%) expression of CD14 and low (less than 25%) expression of CD83.

The results of our optimization as described in the examples below has demonstrated the importance of the delayed addition of cytokines on the expression of especially the CD1a marker.

Furthermore our studies have revealed that it is possible to obtain a yield of about 50% immature dendritic cells with high expression of CD1a marker generated from monocytes, by controlling the initial concentration of monocytes in the seeding population of mononuclear cells.

In a further aspect the present invention therefore relates to a method for optimizing the yield of dendritic cells generated from a sample of mononuclear cells in which method the seeding density of monocytes is between $5 \times 10^6$-$20 \times 10^6$ cells per 25 cm² in 6-8 ml of medium. When using a T25 flask, this means a starting number of monocytes of between $5 \times 10^6$-$20 \times 10^6$ cells. In a particular embodiment the density is between $6 \times 10^6$-$15 \times 10^6$ cells per 25 cm², and more particularly between $8 \times 10^6$-$12 \times 10^6$ cells per 25 cm².

In a particular embodiment at least two allogeneic melanoma cell lines are provided in step a). The number of allogeneic cell lines depends on the number of suitable subclones that have been isolated and screened for the absence of melanocyte differentiation antigens. The more cell lines provided the better are the chances that several immunodominant cancer/testis antigens will be represented in the whole cell lysate. In one embodiment the at least five CT-antigens are provided from at least two allogeneic cell lines. In a particular embodiment the allogeneic cell lines are selected from DDM-1.7 (ECACC 01112339) or DDM-1.13 (ECACC 01112338) (Both cell lines deposited at the European Collection of Animal Cell Cultures, CAMR, GB-Salisbury, Wiltshire SP4 0JG, United Kingdom on 23 Nov. 2001).

Another aspect of the invention relates to the above particular cell lines and also to other cell lines expressing at least five CT antigens and no melanocyte differentiation antigens or substantially no melanocyte differentiation antigens. Accordingly the present invention relates to an isolated melanoma cell line, expressing at least five cancer/testis antigen and no melanocyte differentiation antigens or substantially no melanocyte differentiation antigens, and particularly to the isolated cell lines DDM-1.7 (ECACC 01112339) or DDM-1.13 (ECACC 01112338). Accordingly the present invention also relates to a pharmaceutical composition or a method of the present invention wherein at least one melanoma cell line is selected from the allogeneic cell lines DDM-1.7 (ECACC 01112339) or DDM-1.13 (ECACC 01112338).

The pharmaceutical composition when administered to a human or animal, will induce an immune response in said human or animal resulting in the stimulation of the production of cytotoxic T lymphocytes in the human or animal, and in a further object the invention therefore relates to a method for inducing an immune response in a human or animal comprising the steps:

a) providing at least one cancer cell line expressing cancer/testis antigens and no lineage specific differentiation antigens or substantially no lineage specific differentiation antigens, b) providing autologous dendritic cells from said human or animal, c) culturing said dendritic cells ex vivo in growth medium without any cytokines in an initial growth phase, followed by a second growth phase in medium comprising cytokines, d) loading said dendritic cells from c) with the cancer/testis antigens obtained from a whole cell lysate of the at least one cancer cell line from a), e) administering said loaded dendritic cells from d) to said human or animal.

In a particular embodiment of the above method the cancer cell line is a melanocyte cell line, and the lineage specific differentiation antigens are melanocyte differentiation antigens.

In some cases it will be difficult to provide sufficient amounts of autologous dendritic cells from the patient. In this case it is possible to administer substances that will induce mobilization of CD14+ monocytes prior to step b). Said substances comprise G-CSF and/or GM-CSF.

The dendritic cell precursors, CD14+ monocytes or CD34+ cells, can be obtained from a blood sample, from peripheral blood. It is also possible but not necessary to start from apheresis cells.

Also it is contemplated that the method according to the present invention further comprises the step of administering to the human or animal, a substance that induces activation of T lymphocytes after step e). This could be accomplished by administration of e.g. IL-2 or IL-12.

The present invention also contemplates the use of agents that may increase the level of expression of the cancer/testis antigens before preparing the whole cell lysate of the at least one melanoma cell line. DNA methylation has been suggested to influence the expression level of some testis-specific genes. It has been demonstrated that the demethylating agent 5-aza-2'deoxycytidine (5azaCdR) can induce the expression of the MAGE-A1 gene in MAGE-A1-negative melanoma cells ((De Smet et al., 1996, Proc. Natl. Acad. Sci. U.S.A., v. 93, pp. 7149-7153; Weber et al., 1994, Cancer Res., v. 54, pp. 1766-1771)). 5azaCdR is a cytosine analogue that acts as a suicide substrate for DNA methyltransferase when incorporated into DNA at the target site for DNA methylation, CpG dinucleotides. Demethylation in eukaryotic cells normally leads to increased gene expression in vivo. It has been proposed that MAGE-A1 activation results from the demethylation of the promoter region, following an overall demethylation process, which occurs in many tumors. The activation effect of 5azaCdR on gene expression has also been shown for other members of the MAGE family ((Lucas et al., 1998, Cancer Res., v. 58, pp. 743-752; Lurquin et al., 1997, Genomics, v. 46, pp. 397-408)) and for the GAGE ((De Backer et al, 1999, Cancer Res., v. 59, pp. 3157-3165; Li et al., 1996, Clin. Cancer Res., v. 2, pp. 1619-1625)) and LAGE ((Li et al., 1996, Clin. Cancer Res., v. 2, pp. 1619-1625)) gene families. The role of demethylation in the expression of MAGE genes in tumor cells is supported by the fact that the expression of many other testis-specific genes, whose presence was not detected in tumors, was not upregulated by 5azaCdR treatment ((De Smet et al., 1997, Biochem. Biophys. Res. Commun., v. 241, pp. 653-657)), and among the MAGE-B genes the tumor expression have been detected only for those which are activated by 5azaCdR treatment ((Lurquin et al., 1997, Genomics, v. 46, pp. 397-408)). In addition, a good correlation of the demethylation of CpG sites in the promoter region of the MAGE-A1 gene and the expression of the gene has been observed ((De Smet et al., 1999, Mol. Cell Biol., v. 19, pp. 7327-7335)).

In one embodiment up-regulation of expression of the CT antigens could therefore be done by demethylation of the DNA encoding the CT antigens. In particular this demethylation could be induced by treatment with 5azaCdR. Yet another way of upregulation of CT antigen expression could be inhibition of histone deacetylation. These two types of treatment could be used either separately or in combination. Such treatment may be employed only if cancer/testis antigens remain immunodominant.

Many CT antigens can be grouped into subfamilies that include several members (see Table 1). They are the MAGE-A, MAGE-B, MAGE-C, GAGE, LAGE and SSX subfamilies. For the other antigens only one individual member has been discovered so far. These are the BAGE, SCP-1, TSP50, TRAG-3, SAGE, IL13R alpha, CT9 and CTp11 antigens. All CT antigens could for the purpose of the present invention be considered as potential targets for immunotherapy.

TABLE 1

Human cancer/testis antigens

| Family | Members |
| --- | --- |
| MAGE-A | MAGE-A1, MAGE-A2, MAGE-A3, MAGE-A4, MAGE-A5, MAGE-A6, MAGE-A8, MAGE-A9, MAGE-A10, MAGE-A11, MAGE-A12 |
| MAGE-B | MAGE-B1, MAGE-B2, MAGE-B3, MAGE-B4, MAGE-B5, MAGE-B6, MAGE-B10, MAGE-B16, MAGE-B17 |
| MAGE-C | MAGE-C1, MAGE-C2, MAGE-C3, MAGE-C4, |
| GAGE | GAGE-1, GAGE-2, GAGE-3, GAGE-4, GAGE-5, GAGE-6, GAGE-7, GAGE-8 |
| | PAGE-1, PAGE-2, PAGE-3, PAGE-4 |
| | XAGE-1, XAGE-2, XAGE-3 |
| LAGE | LAGE-1a, LAGE-1b, Ny-ESO-1 |
| SSX | SSX-1, SSX-2, SSX-3, SSX-4, SSX-5 |
| Separate members: | BAGE, SCP-1, TSP50, TRAG-3, SAGE, IL13R alpha, CT9, CTp11 |

One of the largest groups of CT antigens is the group of MAGE proteins, comprising three families, MAGE-A, MAGE-B and MAGE-C.

The MAGE-A genes represent a family of 15 closely related genes located on the long arm of chromosome X (region Xq28) ((Chomez et al., 2001, Cancer Res, v. 61, pp. 5544-5551; De Plaen et al., 1994, Immunogenetics, v. 40, pp. 360-369)), including the first identified gene encoding the antigen MAGE-A1 (previously designated MAGE-1) ((van der Bruggen et al., 1991, Science, v. 254, pp. 1643-1647)). In the majority of the investigated tumors only the expression of the MAGE-A1, -A2, -A3, -A4, -A6 and -A 12 genes has been demonstrated. Recently the expression of other MAGE-A genes, including MAGE-A11 ((Jurk et al., 1998, Int. J. Cancer, v. 75, pp. 762-766)), MAGE-A10 ((Huang et al., 1999, J. Immunol., v. 162, pp. 6849-6854)), MAGE-A5, MAGE-A8 and MAGE-A9 ((Serrano et al., 1999, Int. J. Cancer, v. 83, pp. 664-669)) has also been detected in several tumors.

The ability to present peptide epitopes recognized by cytotoxic T lymphocytes (CTL) has been shown for MAGE-A1 ((van der Bruggen et al., 1991, Science, v. 254, pp. 1643-1647)), MAGE-A2 ((Visseren et al., 1997, Int. J. Cancer, v. 73, pp. 125-130)), MAGE-A3 ((Gaugler et al., 1994, J. Exp. Med., v. 179, pp. 921-930)), MAGE-A4 ((Duffour et al., 1999, Eur. J. Immunol., v. 29, pp. 3329-3337)), MAGE-A6 ((Tanzarella et al., 1999, Cancer Res., v. 59, pp. 2668-2674)), MAGE-A10 ((Huang et al., 1999, J. Immunol., v. 162, pp. 6849-6854)) and MAGE-A 12 ((Panelli et al., 2000, J. Immunol., v. 164, pp. 4382-4392)). T-helper cells can also recognize MAGE antigens, and corresponding epitopes of MAGE-A1 and MAGE-A3 antigens have been identified ((Chaux et al., 1999, J. Exp. Med, v. 189, pp. 767-778; Chaux et al., 2001, Eur J Immunol, v. 31, pp. 1910-1916; Manici et al., 1999, J. Exp. Med., v. 189, pp. 871-876)).

MAGE expression has been detected in many types of human malignancies. Cutaneous melanomas have the highest level of MAGE expression (up to 65% for MAGE-A3) ((De Plaen et al., 1994, Immunogenetics, v. 40, pp. 360-369)), while ocular melanomas usually are negative for MAGE expression ((Mulcahy et al., 1996, Int. J. Cancer, v. 66, pp.

738-742)). To a lesser extent MAGE antigens are expressed in other types of tumors such as mammary carcinomas, head and neck tumors, lung carcinomas, sarcomas and bladder carcinomas (for review see (van Pel et al., 1995, Immunol. Rev., v. 145, pp. 229-250)). A high expression of MAGE-A1 (80%) was found in hepatocarcinomas ((Yamashita et al., 1996, Hepatology, v. 24, pp. 1437-1440)). MAGE-A4, in contrast to other MAGE-A antigens, is expressed in significant proportions of lymphomas, including Hodgkin's lymphomas, where its expression is restricted to Reed-Sternberg cells ((Chambost et al., 2000, Blood, v. 95, pp. 3530-3533)). When a tumor sample is found to be positive for MAGE-A4, the gene is usually expressed at very high levels.

The MAGE-B genes represent a family of 17 genes located in the regions p21.3 and p22 of the X chromosome, with 8 of them being pseudogenes ((Chomez et al., 2001, Cancer Res, v. 61, pp. 5544-5551; Lucas et al, 2000, Int. J. Cancer, v. 87, pp. 55-60; Lurquin et al., 1997, Genomics, v. 46, pp. 397-408)). Only two genes, MAGE-B1 and MAGE-B2, are expressed in a significant fraction of tumors of various histological types. The expression of MAGE-B5 and MAGE-B6 was detected in a limited number of tumor samples ((Lucas et al., 2000, Int. J. Cancer, v. 87, pp. 55-60)).

The seven members of the MAGE-C family are located in the Xq26-q27 region. The MAGE-C1 gene has been identified by analysis of the selective gene expression in testis and melanomas ((Lucas et al., 1998, Cancer Res., v. 58, pp. 743-752)). Its expression pattern strongly resembles the expression pattern of the MAGE-A genes. Another gene CT7 ((Chen et al., 1998, Proc. Natl. Acad. Sci. U.S.A., v. 95, pp. 6919-6923)), probably represent a different MAGE-C1 allele. MAGE-C2/CT10 is localized in the Xq27 region but in contrast to MAGE-C1, this protein has no repetitive portion. The third and forth members, MAGE-C3 and MAGE-C4, were identified by database searching ((Chomez et al., 2001, Cancer Res, v. 61, pp. 5544-5551; Lucas et al., 2000, Int. J. Cancer, v. 87, pp. 55-60)).

Several non-MAGE proteins with characteristics of cancer/testis antigens have been described. One of these was the BAGE antigen ((Boël et al., 1995, Immunity, v. 2, pp. 167-175)). Its pattern of expression in tumor samples is very similar to the expression pattern of the MAGE antigens, with an overall lower frequency of expression (22% in melanomas, 15% in bladder carcinomas, 10% in mammary carcinomas and 8% in head and neck squamous cell carcinomas). As for the MAGE antigens, the expression of BAGE correlates with the stage of tumor progression. The BAGE antigen could be recognized by CTL's, and antigenic peptide epitopes were identified.

An additional antigen was identified as a HLA-Cw6-restricted epitope encoded by the GAGE-1 gene ((Van den Eynde et al., 1995, J. Exp. Med., v. 182, pp. 689-698)). This gene belongs to a large family of genes, including the GAGE-1-GAGES-8 genes ((Chen et al., 1998, J. Biol. Chem., v. 273, pp. 17618-17625; De Backer et al., 1999, Cancer Res., v. 59, pp. 3157-3165; Van den Eynde et al., 1995, J. Exp. Med., v. 182, pp. 689-698)), the PAGE-1-PAGE-4 genes ((Brinkmann et al., 1998, Proc. Natl. Acad. Sci. U.S.A., v. 95, pp. 10757-10762; Chen et al., 1998, J. Biol. Chem., v. 273, pp. 17618-17625)), and the XAGE-1-XAGE-3 genes ((Brinkmann et al., 1999, Cancer Res., v. 59, pp. 1445-1448)). The two genes of the GAGE family that encode a protein, GAGE-1 and GAGE-2, are expressed in a significant proportion of melanomas (24%), sarcomas (25%), non-small lung cancers (19%), head and neck tumors (19%), and bladder tumors (12%).

Several CT antigens have been identified recently using the SEREX method (serological expression cloning of recombinant cDNA libraries of human tumors) ((Sahin et al., 1995, Proc. Natl. Acad. Sci. U.S.A., v. 92, pp. 11810-11813)). One of them, NY-ESO-1, encoded by the CTAG gene ((Chen et al., 1997, Cytogenet. Cell Genet., v. 79, pp. 237-240)), was expressed in 23 of 67 melanoma specimens, 10 of 33 breast cancers, 4 of 16 prostate cancers, 4 of 5 bladder cancers, as well as a proportion of other tumor types, but only in 2 of 11 cultured melanoma cell lines ((Chen et al., 1997, Proc. Natl. Acad. Sci. U.S.A., v. 94, pp. 1914-1918)). In a melanoma patient, the CTL response was restricted by HLA-A2, and three peptides recognized by a melanoma-specific CTL line have been identified. This antigen was also found to induce a HLA-A31-restricted CTL response in one melanoma patient ((Wang et al., 1998, J. Immunol., v. 161, pp. 3596-3606)). In addition, MHC class II restriction by CD4+ T lymphocytes has been described, with identification of three peptide epitopes ((Jäger et al., 2000, J. Exp. Med., v. 191, pp. 625-630)). A gene homologous to CTAG, has recently been described. This gene, LAGE-1 ((Lethé et al., 1998, Int. J. Cancer, v. 76, pp. 903-908)) has a distribution in different tumors similar to NY-ESO-1. Both genes are located in the q28 band of the X chromosome, close to the MAGE genes ((Lethé et al., 1998, Int. J. Cancer, v. 76, pp. 903-908)). NY-ESO-1 is one of the most immunogenic tumor antigens identified to date.

Accordingly in a further embodiment of the present invention the cancer/testis antigens comprise antigens selected from the MAGE-A, MAGE-B, MAGE-C, GAGE, LAGE, SSX subfamilies.

In a particular embodiment the CT antigens comprise antigens selected from MAGE-A1, MAGE-A2, MAGE-A3, MAGE-A4, MAGE-A5, MAGE-A6, MAGE-A8, MAGE-A9, MAGE-A 10, MAGE-A11, MAGE-A 12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-C4, BAGE, GAGE-1, GAGE-2, GAGE-3, GAGE-4, GAGE-5, GAGE-6, GAGE-7, GAGE-8, NY-ESO-1, LAGE, PAGE-1, PAGE-2, PAGE-3, PAGE-4, XAGE-1, XAGE-2, XAGE-3, SSX-1, SSX-2, SSX-3, SSX-4, SSX-5. And in another particular embodiment the CT antigens comprise antigens selected from SCP-1, TSP-50, TRAG-3, SAGE, IL-13R alpha, CTp11.

In a still further particular embodiment the CT antigens comprise antigens selected from MAGE-A1, MAGE-A3, MAGE-A4, MAGE-A6, MAGE-A10, MAGE-A12, and NY-ESO-1.

The above antigens represent antigens that are considered to be particularly useful in the context of the present invention, however, other antigens not specifically mentioned could also be used as long as a multiplicity of cancer/testis antigens are used, and particularly at least five, more particularly at least 6, and even more particularly at least seven CT antigens.

A further embodiment of the present invention relates to a use of the above composition as an immunotherapeutic vaccine for the treatment of cancer.

One condition for employment of melanoma cell-based compositions or vaccines is the presence in a host of a malignancy at advanced stages of disease. Another condition could be presence of primary tumor, and in this case the aim of treatment is not only to induce rejection of the primary tumor, but also to prevent development of metastases, since a group of CT antigens is predominantly expressed in metastases. Yet another condition could be removal of primary or metastatic tumor by other means (surgery, irradiation), and in this case the aim of treatment is the prevention of tumor recurrence.

Tumors that express several CT antigens have higher chances of being rejected or restricted in growth than tumors that have no or only one CT antigen. Therefore, determination of expression of CT antigens in tumor biopsy may be of significance in predicting the effectiveness of employment of a universal melanoma cell-based vaccine.

EXAMPLES

In the following the present invention will be further illustrated by way of several non-limiting embodiments.

Example 1

Isolation of Melanocyte Differentiation Antigen Deficient Clones of the DDM-1 Melanoma Cell Line DDM-1 melanoma cell lines obtained from a patient with a long disease free period. DDM-1 melanoma cells were cloned, and 8 clones were screened and found to be negative for the expression of tyrosinase. Tyrosinase is one of the known melanocyte differentiation antigens. These clones (DDM-1.5, DDM-1.6, DDM-1.7, DDM-1.10, DDM-1.11, DDM-1.13, DDM-1.24, and DDM-1.25) were further tested for the expression of two immunodominant melanocyte differentiation antigens, gp100 and Melan A/MART-1.

Melanoma cells were routinely cultured in T75 tissue culture flasks (Nunc) in 20 ml of RPMI 1640 medium (BioWhittaker) supplemented with 10% of foetal calf serum. For use in experiments on induction of immune response against dendritic cells loaded with melanoma cell lysate, cell growth was adapted to medium containing 2% human serum (HuS). Cells were harvested by removal of medium from the culture flask and addition of 5 ml of 0.02% EDTA in Ca, Mg-free PBS (BioWhittaker), incubation in $CO_2$-incubator for 10-20 min, addition of 10 ml of PBS and transfer of detached cells into a centrifuge tube. After centrifugation at 200 g for 5 min, the supernatant was discarded, and the pellet was resuspended in culture medium, cells were counted, and $1.5 \times 10^6$ cells were placed into T75 flask in 20 ml of culture medium.

Expression of gp100 and Melan-A/MART-1 antigens was tested by determination of the sensitivity of melanoma cells to lysis induced by cytotoxic T lymphocyte (CTL) clones specific against these antigens. We have described the properties of these CTL clones previously (Kirkin et al., 1999, Cancer Immunol. Immunother., v. 48, pp. 239-246). Melanoma cells were harvested as described above, resuspended in culture medium, counted, and $0.5 \times 10^6$ cells of each clone were transferred into an 11-ml conical tube (Nunc). Cells were spun down at 200 g for 5 min, the supernatant was discarded, and the pellet was resuspended in 0.1 ml of culture medium. 0.1 ml of $Na_2CrO_4$ solution (0.1 mCi, Amersham) was added, and cells were incubated in a water bath at 37° C. for 60 min. After washing three times with RPMI-1640, the targets were adjusted to a concentration at $5 \times 10^4$ cells/ml in RPMI-1640 with 10% FCS. The cytotoxic lymphocytes were used at concentration of $5 \times 10^5$ cells/ml. CTLs and target melanoma cells were seeded in 100 µl aliquots in triplicates in 96 U-bottomed microtiter plates (Nunc), spun down at 200 g for 2 min and incubated at 37° C. in 5% $CO_2$. After 4 hours plates were spun down at 250 g for 3 min, 100 µl supernatant was harvested and the radioactivity was determined (Cobra 5005, Packard Instruments, Meriden, Conn., USA). The specific lysis was calculated according standard formula. Results of one representative experiment are shown in FIG. 1. From these results it follows that only two of the investigated melanoma clones, DDM-1.7 and DDM-1.13, are completely resistant to lytic attack by CTLs, indicating possible loss of the expression of the indicated melanocyte differentiation antigens in these melanoma clones.

In order to get additional proof for the loss of antigen expression, we conducted analysis of expression of RNA coding for these proteins by RT-PCR analysis. $2 \times 10^6$ cells were spun down, the supernatant was discarded, and the pellet was solubilized in 0.3 ml of Cell Lysis Solution (Purescript® RNA isolation kit, Gentra). RNA was isolated according to the manufacturer's instructions, precipitated by adding two volumes of 100% isopropanol over the lysis solution, washed with 70% ethanol and re-hydrated in 10 µl RNAase-free distilled water. The isolated RNA was treated by DNAase to destroy any trace amount of DNA in the preparation. For this purpose, the reagents from DNA-free™ kit (Ambion) were used. 1 µl 10× DNAase buffer and 1 µl DNAase (2 units) were added to the sample, the mixture was incubated for 30 min at 37° C., and reaction was terminated by addition of 1.2 µl DNAase inactivation reagent cDNA synthesis was performed by reverse transcription in 20 µl total volume using 10 µl RNA. For this purpose, Super Script II RT primed with oligo (dT) (Gibco BRL) was used according to the manufacturers' protocol. Incubation was performed at 42° C. for 30 min, followed by 45° C. for 30 min and 72° C. for 2 min. 1 µl cDNA was used in the PCR amplification containing the following in 1×PCR buffer: 50 mM KCl, 10 mM Tris/HCl (pH 9.0), 1.5 mM Mg $Cl_2$, 0.2 mM cresol, 12% sucrose, 0.005% bovine serum albumin, 2.5 pmol of each primer, 40 µM of dNTPs (Pharmacia LKB), and 1.25 U (1 µl) of AmpliTaq polymerase (Perkin-Elmer). The primers were selected in such a way that the product of amplification could be efficiently cumulated at the same reaction conditions, thus, enabling us to compare expression in the tumor cells of a variety of selected antigens in simultaneously performed reactions. Sequences of primers used in these experiments and in experiments described below are presented in Table 2. In all reactions, a "hot start" procedure was used in which Taq polymerase and dNTPs were added to the reaction tube at an 80° C. step between the denaturation and annealing steps of the first cycle. The parameters used for the amplification were 30-38 cycles (94° C. for 30 sec, 60° C. for 30 sec, and 72° C. for 40 sec) followed by 10 min at 72° C. and cooling to 4° C. Amplifications were performed on a Perkin-Elmer GeneAmp PCR System 9600. Negative controls contained aliquots of water instead of cDNA. GAPDH was amplified as a positive control for the reaction as well as to give an estimation of the rate of expression of the antigens relative to this household gene. Negative results were repeated at least twice, with an increased number of cycles. The products of amplification were separated by electrophoresis through 2% agarose gel at 100V, stained with ethidium bromide, visualized under UV illumination and recorded by an image recording system. When performing semi-quantitative RT-PCR, the number of cycles was reduced to 22, which ensured a linear increase in the amount of the selected sequences with the number of amplification cycles. The PCR reaction was conducted using 3- or 5-fold dilutions of the cDNA template. The intensity of the resulting product bands after electrophoretic separation was analyzed by image analysis, normalized by intensity of the GAPDH product obtained using the same template and at the same dilutions, and the level the corresponding RNA transcripts was compared in different cell lines.

TABLE 2

Oligonucleotide sequences 5'-3'

| Gene | Primer | |
|---|---|---|
| GADPH | Sense | AGGGGGGAGCCAAAAGGG (SEQ ID NO: 1) |
| | Anti-sense | GAGGAGTGGGTGTCGCTGT (SEQ ID NO: 2) |
| Gp100 | Sense | GGCTGGTGAAGAGACAAGTCC (SEQ ID NO: 3) |
| | Anti-sense | AGAGATGCAAGGACCACAGCC (SEQ ID NO: 4) |
| Mart-1 | Sense | GAAGGTGTCCTGTGCCCTGACCC (SEQ ID NO: 5) |
| | Anti-sense | GGCTTGCATTTTTCCTACACCATTCC (SEQ ID NO: 6) |
| MAGE-A1 | Sense | GATTCCCTGGAGGCCACAG (SEQ ID NO: 7) |
| | Anti-sense | CCTCACTGGGTTGCCTCTGTC (SEQ ID NO: 8) |
| MAGE-A3 | Sense | ACCAGAGGCCCCCGGAGGAG (SEQ ID NO: 9) |
| | Anti-sense | CTGCCAATTTCCGACGACACTCC (SEQ ID NO: 10) |
| MAGE-A4 | Sense | GAGCAGACAGGCCAACCG (SEQ ID NO: 11) |
| | Anti-sense | AAGGACTCTGCGTCAGGC (SEQ ID NO: 12) |
| MAGE-A6 | Sense | AGGACCAGAGGCCCCC (SEQ ID NO: 13) |
| | Anti-sense | GGATGATTATCAGGAAGCCTGT (SEQ ID NO: 14) |
| MAGE-A10 | Sense | CACAGAGCAGCACTGAAGGAG (SEQ ID NO: 15) |
| | Anti-sense | CTGGGTAAAGACTCAGTGTCTGG (SEQ ID NO: 16) |
| MAGE-A12 | Sense | TGGAAGTGGTCCGCATCG (SEQ ID NO: 17) |
| | Anti-sense | GCCCTCCACTGATCTTTAGCAA (SEQ ID NO: 18) |
| NY-ESO-1 | Sense | GGCACAGGGGGTTC (SEQ ID NO: 19) |
| | Anti-sense | GCTTAGCGGCCTCTGCCCT (SEQ ID NO: 20) |

Figure 2:
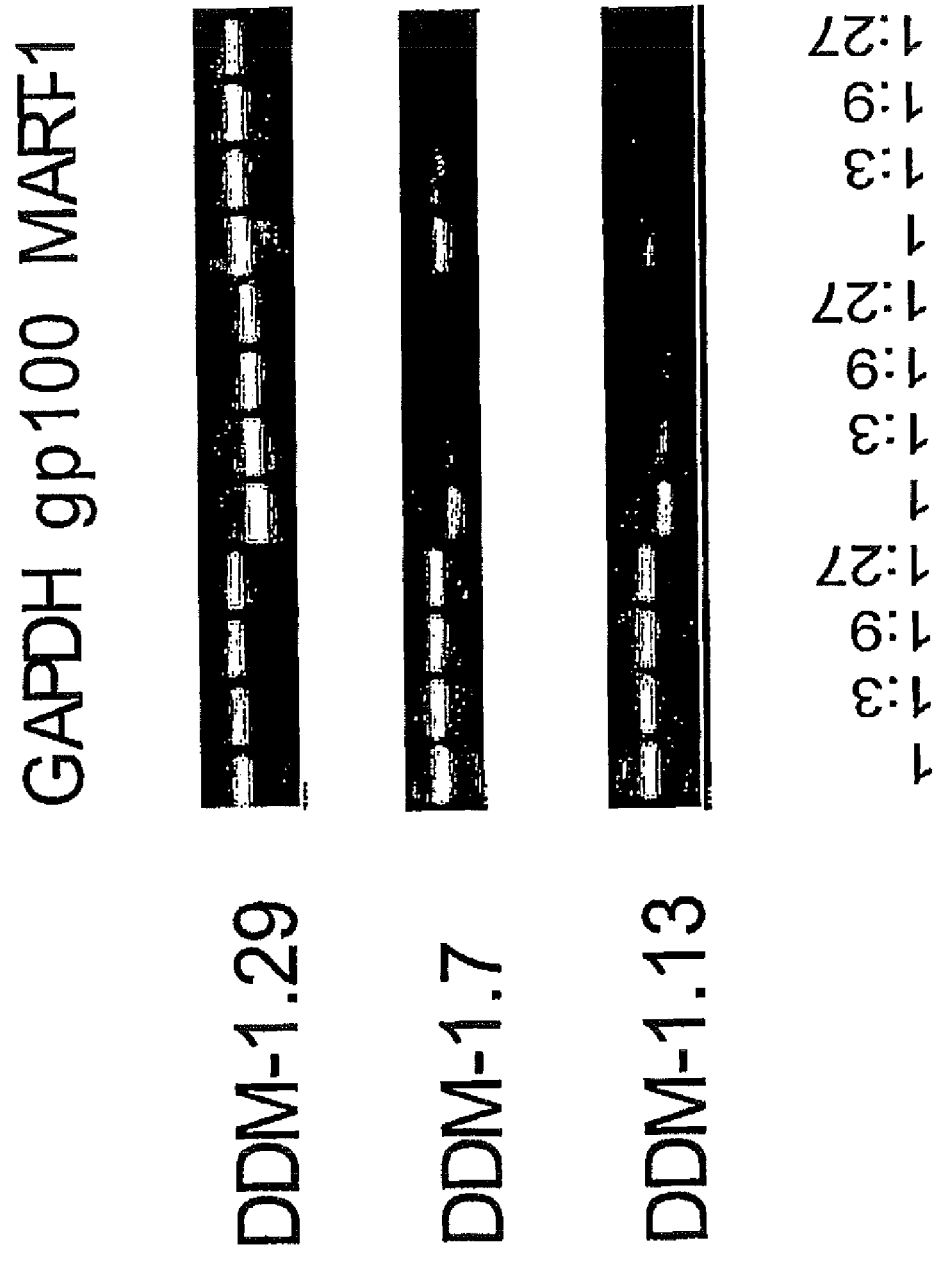
FIG. 2 shows expression of melanocyte differentiation antigens gp100 and MART-1/Melan A in three melanoma cell clones, DDM-1.7, DDM-1.13, and DDM-1.29 analyzed by RT-PCR.

The results of determination of expression of the melanocyte differentiation antigens gp100 and MART-1 in 3 melanoma cell clones, DDM-1.7, DDM-1.13 and DDM-1.29, shown in FIG. 2, clearly demonstrate that the level of RNA transcripts in the DDM-1.7 and DDM-1.13 melanoma clones grown in 10% FCS is also much lower than in DDM-1.29 and the intensity of the corresponding product bands declines with serial dilutions of cDNA template much more rapidly for DDM-1.7 and DDM-1.13 as compared to DDM-1.29. According to semi-quantitative RT-PCR and after normalization of the data by the transcription level of housekeeping GADPH, the level of the melanocyte antigens' RNA transcripts in DDM-1.7, DDM-1.13 was less than 1% of the corresponding level in DDM-1.29. After adaptation of the cells to the growth in 2% human serum, a slight increase in the expression of the melanocyte differentiation antigens (not shown) could be seen by RT-PCR that did not exceed 1% of the corresponding level in DDM-1.29.

Expression of gp100 in the cells adapted to the growth in 2% human serum was also investigated by immunostaining. For this, cells have been cultured on glass cover slips placed into petri dishes. After rinsing with cold PBS, cells have been fixed with ice-cold mixture of methanol-acetone (1:1) for 15 min. After drying, cover slips were incubated in PBS for 1 min and stained according to standard procedure known in the art using as the first antibody a mixture of antibodies HMB45 and HMB50 (NeoMarkers), as second antibodies—biotinylated sheep anti-mouse Ig antibodies (Amersham), and as third reagent—streptavidin-Texas red (Amersham). As seen from FIG. 3, no staining could be seen in DDM-1.7 cells, compared to the intensive staining detected in DDM-1.29 cells. Visualization of a large number of cells showed that a very small population of the cells (less than 1%) was positive in the DDM-1.7 culture (not shown). Among DDM-1.13 cells grown in the same conditions, about 1% of cells was positively stained for gp100 (not shown).

Figure 4:
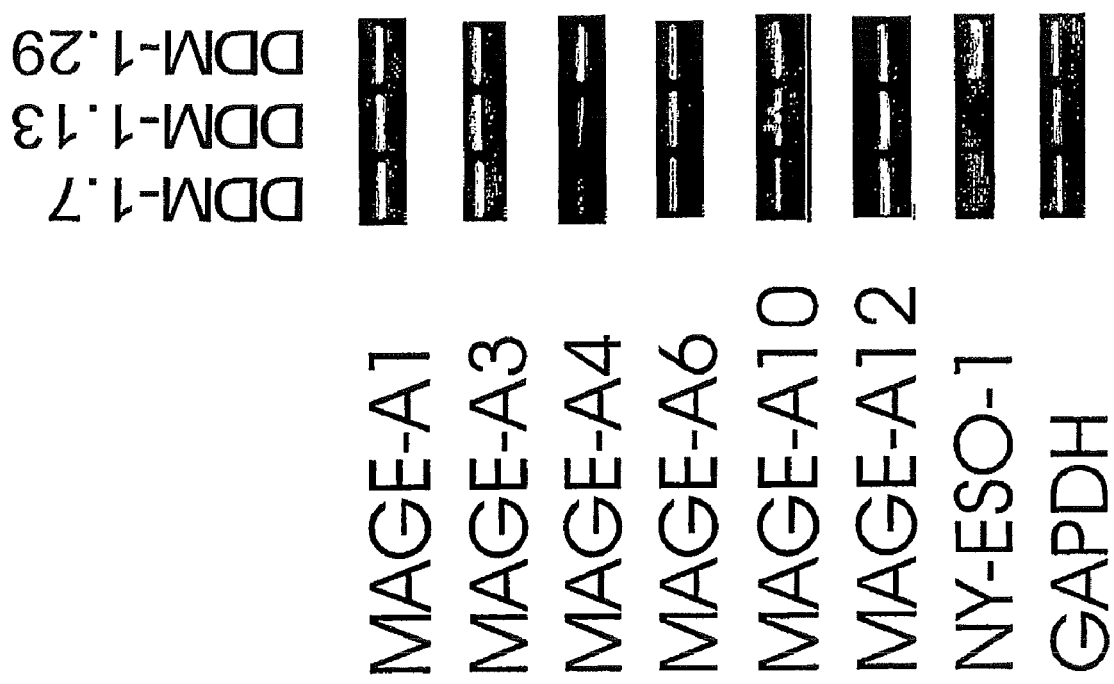
FIG. 4 shows expression of MAGE-A1, MAGE-A3, MAGE-A4, MAGE-A6, MAGE-A 12, NY-ESO-1 and GAPDH in the three melanoma cell clones, DDM-1.7, DDM-1.13, and DDM-1.29 analyzed by RT-PCR analysis.

To determine levels of expression of MAGE-A and NY-ESO-1 antigens, we conducted RT-PCR reactions using primers for these antigens (sequences of primers are presented in Table 2). The results of comparison of expression of mRNA coding for MAGE-A1, MAGE-A3, MAGE-A4, MAGE-A6, MAGE-A 10, MAGE-A12 and NY-ESO-1 proteins are presented in FIG. 4. DDM-1.29 expresses all tested antigens, while DDM-1.7 and DDM-1.13 express only 4-5 of them.

Figure 5:
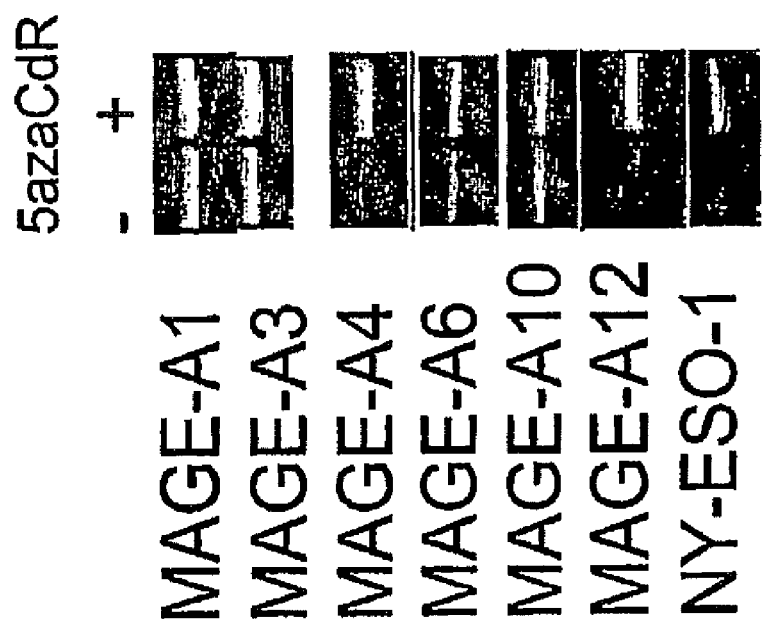
FIG. 5 shows expression of MAGE-A and NY-ESO-1 in DDM-1.13 cells after treatment with the DNA-demethylating agent 5-aza-2'-deoxycytidine.

Expression of CT antigens is known to be up-regulated by treatment of cells with the DNA de-methylating agents 5-aza-2'-deoxycytidine. We decided to test, if expression of MAGE-A and NY-ESO-1 proteins could be up-regulated in the DDM-1.13 melanoma cell clone by such treatment. Cells were seeded in T25 culture flasks, and after 24 hours, 5-aza-2'-deoxycytidine was added at final concentration of 1 µM. Cells were incubated 3 days, then medium was changed, and after additional incubation for two days, cells were harvested as described above. Determination of antigen expression was done as described above, and the results, presented in FIG. 5, demonstrate that after treatment of cells with 5-aza-2'-deoxycytidine the expression increased for all tested CT antigens.

Example 2

Generation of Dendritic Cells with Increased Abilities to Present Exogenous Proteins The unique property of dendritic cells is that they can present exogenous proteins for recognition by CD8$^+$ CTLs. Maximal ability to uptake exogenous proteins is associated with the immature stage of DC differentiation. However, data on direct association between phagocytic activity of DC and their ability to present up-taken antigens for recognition by CTLs specific against these antigens, are absent. Therefore we conducted experiments aiming: a) to optimise generation of immature dendritic cells with high ability to uptake exogenous proteins and b) to demonstrate correlation between phagocytic activity of dendritic cells and their ability to present antigens from exogenously added melanoma lysate.

In the first set of experiments we optimized generation of phagocytic dendritic cells by varying time of lymphokine addition and use of TGF-beta 1, which was shown to improve generation of dendritic cells from monocytes of peripheral blood (Yang et al., 1999, J. Immunol., v. 163, pp. 1737-1741). Dendritic cells were typically generated from 50 ml of peripheral blood of HLA-A2-positive donors containing 25 IU/ml of heparin. Blood was split in two 50-ml tubes containing 12.5 ml of Ca, Mg-free PBS (named below as PBS), and applied on Lymphoprep (12.5 ml placed into two 50-ml tubes). After centrifugation (800 g, 25 min), 10 ml of upper layer were taken into a syringe, passed through a 0.2 µm filter and used as a source of plasma. Mononuclear cells were harvested from the interphase layer, and after at least two-fold dilution with PBS, spun down 6 times, first at 650 g, 10 min, then at 450 g, 7 min, and afterwards at 250 g, 5 min. After each centrifugation, the supernatant was discarded, and the pellet was re-suspended in 5 ml of PBS until complete disappearance of cell aggregates. Fresh PBS was added to fill tube to the top, and centrifugation was repeated. After last centrifugation, pellet was re-suspended in 5 ml of adhesion medium, consisting of RPMI 1640 medium with addition of 2% of plasma, and after counting, cell concentration was adjusted to $5 \times 10^6$/ml. 3 ml of cell suspension were placed into the wells of a 6-well plate (Falcon, non-TC treated), totally 4 wells, and incubated in $CO_2$-incubator for 1.5 hours. After this incubation, non-adherent cells were collected, and monolayer of adherent cells was washed twice with warm RPMI 1640 medium, and 3 ml of culture medium consisting of RPMI medium with addition of 1% of plasma (DC medium). Recombinant human GM-CSF and IL-4 at concentration of 1000 U/ml were added into two wells (cultures 1 and 3). After overnight incubation, medium was completely changed in two wells (cultures 2 and 4). For this, medium was collected into one centrifuge tube, and 2.5 ml of new pre-warmed DC medium was added into each well. Collected cells were spun down (250 g, 5 min), supernatant was discarded, pellet was re-suspended in 1 ml of pre-warmed DC medium, and 0.5 ml of cell suspension were placed back into cultures 2 and 4. To cultures 3 and 4, TGF-beta 1 was added at final concentration of 100 ng/ml.

After additional 5 days, phagocytic activity of generated dendritic cells was detected. RPMI 1640 medium containing 10% FCS (fetal calf serum) was placed into several wells of a flat-bottom non-TC-treated 96-well plate (Falcon) as well as in centrifuge tubes for 30-60 min. 0.5 ml of each DC culture was transferred into pre-treated centrifuge tubes, and after centrifugation (200 g, 5 min) the supernatant was discarded, and pellets were re-suspended in 0.5 ml of DC medium. Medium was removed from wells of the 96-well plate, and 0.2 ml of each cell suspension was added into wells, two wells for each type of culture. 10 μl of stock solution of FluoSpheres were added to each tube, and plate was placed into $CO_2$-incubator. After 4 hours, cultures were harvested into centrifuge tubes pre-treated as described above, and after two washings by centrifugation at 200 g, 5 min, in RPMI 1640 medium with 10% FCS, pellets were resuspended in 25 μl of RPMI medium Tubes were place into ice. 5 μl of cell suspension were place on microscope glass slides, and slides were places into moist chamber (usually large petri dishes with moisten paper were employed) and incubated 10-15 min in $CO_2$-incubator. After this, a drop of cell suspension was covered by a 13-mm glass cover slip, and cells were observed under fluorescent microscope. Using digital camera Leica DC100, images were transferred to computer and were stored as bitmap files.

Results of one experiment on determination of phagocytic activity of dendritic cells generated under investigated conditions are presented in FIG. 6. It is clearly seen that addition of GM-CSF and IL-4 the day after start of the culture together with total medium change has significant advantages in comparison to cultures where GM-CSF and IL-4 were added from the start of cultures. It should be noted that in majority of papers describing establishment of dendritic cells for use in immunization in combination with tumor cell lysates, lymphokines were added from the start of cultures (see, for example, (Chakraborty et al., 1998, Cancer Immunol. Immunother., v. 47, pp. 58-64; Nestle et al., 1998, Nature Med., v. 4, pp. 328-332)).

Results presented in FIG. 6 also demonstrate that TGF-beta 1, that was used by investigators as additional lymphokine during generation of dendritic cells (Yang et al., 1999, J. Immunol., v. 163, pp. 1737-1741), has no enhancing effect on phagocytic activity of dendritic cells, and in fact, decreased phagocytic activity in a number of experiments (not shown).

Ability to present antigenic peptides from exogenously added proteins was investigated using a model of recognition of dendritic cells loaded with lysate of DDM-1.29 cells, having high levels of expression of the melanocyte differentiation antigen gp100, by gp100-specific CTLs established by us (Kirkin et al., 1999, Cancer Immunol. Immunother., v. 48, pp. 239-246) and used in example 1 for detection of expression of this antigen in different melanoma cell clones.

A lysate of DDM-1.29 cells was prepared as described below. Melanoma cells cultured as described in example 1, washed twice with PBS, and re-suspended in RPMI 1640 medium (Gibco) at $10^7$ cells/ml. Cells were subjected to five cycles of freezing (liquid nitrogen)—thawing, sonicated 15 min in a ultrasound bath (Metason 200, Struer), then spun down, first at 800 g, for 15 min at 4° C., then at 13000 g, for 60 min at 4° C. The supernatant was collected, filtrated through 0.2 μm filter, and protein concentration was determined using the bicinchoninic acid protein assay reagent (Pierce) according to the procedure given by the manufacturer. The protein concentration was in the range of 3.5-5 mg/ml. Aliquots of supernatant were stored frozen at −80° C.

To load dendritic cells with tumor lysate, different dendritic cell cultures were transferred into centrifuge tubes, spun down, and after discarding of supernatants pellets were re-suspended in 2 ml of DC medium, cells were counted, and cell suspension was diluted up to $5 \times 10^5$/ml. 1.8 ml of cell suspension were placed into well of Falcon non-TC-treated 24-well plate, and 0.2 ml of tumor lysate were added together with GM-CSF and IL-4 (1000 U/ml of each). After overnight incubation, 20 ng/ml of TNF-alfa were added. After additional incubation for 24 hours, cultures were harvested by intensive pipetting, transferred into pre-treated centrifuge tubes, spun down at 200 g, for 5 min, and supernatants were decanted, and pellets were resuspended in 2 ml of DC medium. After counting, the cell suspension was diluted to $3 \times 10^5$ cells/ml, and 1 ml of cell suspension was placed in wells of 24-well TC plate (Nunc), two wells for each type of dendritic cells culture. To one of the wells 1 ml of medium was added, and to another 1 ml of CTL suspension ($10^6$/ml). Cultures were incubated for 24 hours, after which 1 ml of supernatant was transferred into an eppendorf tube, spun down, and the supernatant was transferred into another eppendorf tube, and analysis of amount of produced interferon gamma (IFN-γ) was performed by ELISA method as follows. Immunoplate MaxiSorp plates (Nunc) were coated with 100 μl of anti-human IFN-γ purified monoclonal antibody (Endogen) diluted to 2 μg/ml in coating buffer (PBS, pH 7.4) by incubating overnight at room temperature. The coating solution was removed, 200 μl of blocking solution (4% BSA in PBS) was added, and incubated for 1 hour at room temperature. Plates were washed four times with PBS supplemented with 0.05% Tween-20 (washing buffer), and 50 μl of two-fold standard dilutions of the standard (recombinant IFN-γ, Endogen) in the culture medium, ranging from 15 to 1000 pg/ml, were added in duplicate. The collected supernatants were centrifuged at 3,000 g for 5 min, and 50 μl of the samples and two two-fold dilutions applied in triplicate. Plates were incubated overnight at 4° C. Without washing the plate, 50 μl of biotin-labelled detecting anti-body (anti-IFN-γ biotin-labelled, Endogen) diluted to 0.5 μg/ml in the blocking solution was added, and incubation continued for 2 hours at room temperature. After four-fold washing with the washing buffer, 100 μl/well of HRP-conjugated streptavidin (Genzyme) 1:1000 diluted in the blocking buffer was added and the plates incubated for 1 hour at room temperature. The plates were washed four times with the wash buffer and blotted on a paper towel. 100 μl of the substrate solution (5 mg OPD was dissolved in 11 ml citrate buffer and supplemented with 5 μl of hydrogen peroxide) was added to each well. The reaction developed during 15-40 min at room temperature and was terminated by adding 50 μl of 10% sulphuric acid. The differential absorbance was measured on an ELISA reader as a difference between the values at 490 and 650 nm. The control values where only cell medium was added instead of IFN-γ, were subtracted, and concentration of the released in the experiment IFN-γ was determined and expressed in pg/ml using the IFN-γ calibration curve plotted from the same experiment.

Figure 7:
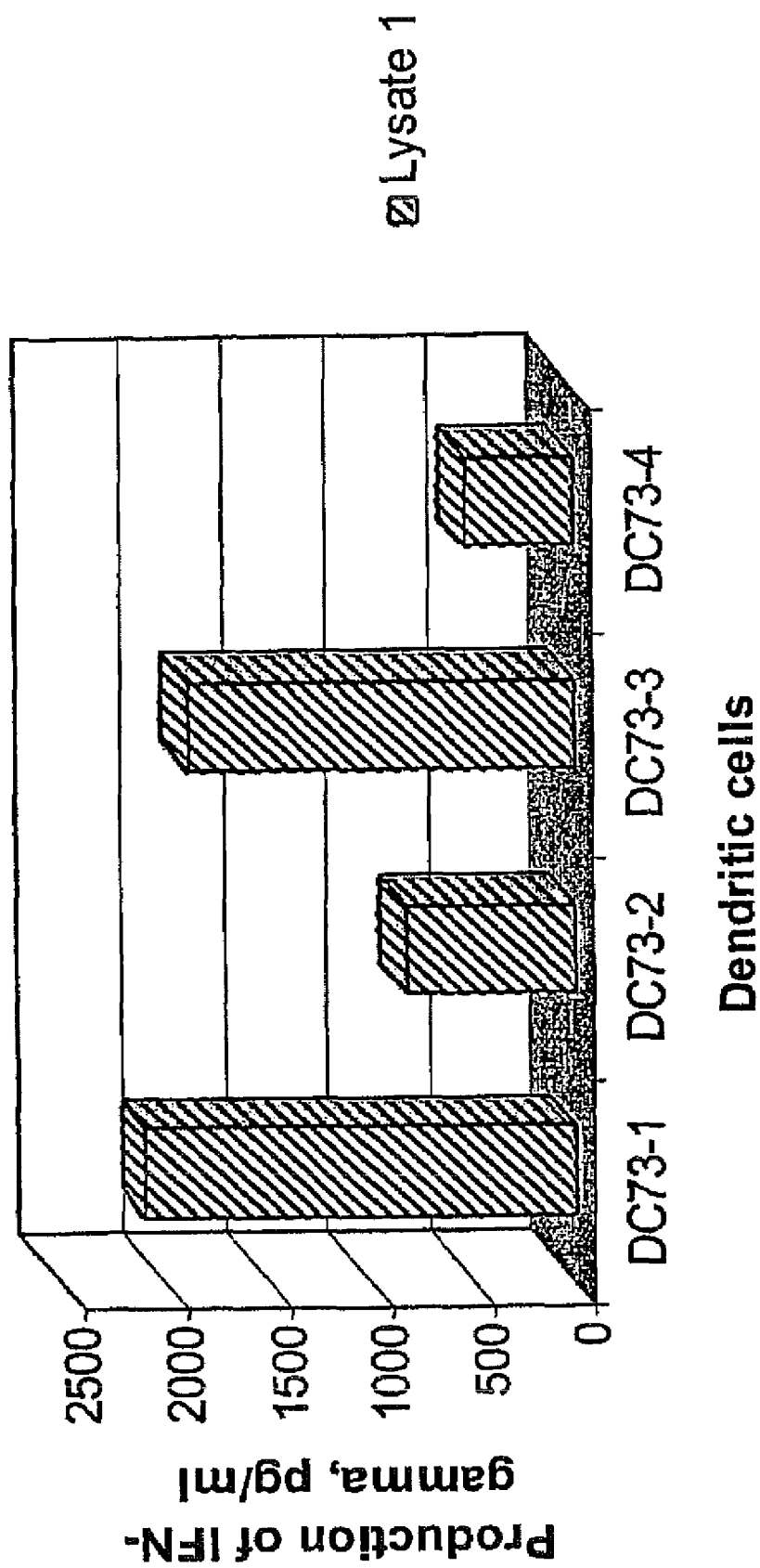
FIG. 7 shows production of IFN-γ by a gp100-specific CTL clone after interaction with four dendritic cell cultures (same as in FIG. 6) loaded with lysate of DDM-1.29 cells.

FIG. 7 presents data of one of these experiments. It could be seen that maximal specific production of IFN-γ, representing difference between IFN-γ production in the presence of lysate-loaded dendritic cells and "empty" dendritic cells, is maximal for dendritic cell cultures 1 and 3, the same cultures that have maximal phagocytic activity.

In summary, the ability of dendritic cells to specifically stimulate CTLs with antigens uptaken from tumor cell lysate correlates with phagocytic activity of dendritic cells, is independent of the presence of TNF-α during DC differentiation, and is maximal in DC cultures in which addition of GM-CSF and IL-4 was delayed for 1 day and was associated with a complete medium change.

Example 3

Development of Cytotoxic T Lymphocytes with Broad Anti-Tumor Activity after Stimulation of Peripheral Blood Lymphocytes of Normal Donors with Autologous Dendritic Cells Loaded with Melanoma Cell-Derived Lysate The ability of dendritic cells loaded with melanoma cell lysate to stimulate development of cytotoxic T lymphocytes specific against tumor antigens was tested in vitro in mixed lymphocyte dendritic cell culture. Dendritic cells were generated from peripheral blood of normal HLA-A2-positive donors as described in Example 2. After initial step of adsorption of monocytes, non-adsorbed lymphocytes were collected and frozen down in autologous plasma plus 10% DMSO for later use. Dendritic cells loaded with tumor lysate were harvested, irradiated (6000 Rad), washed, re-suspended in X-VIVO 15 medium supplemented with 1% of autologous plasma (complete medium) at $3 \times 10^5$/ml and placed into five wells of 24-well plates, 1 ml into each well. The rest of the dendritic cells was frozen in pooled human serum containing 10% DMSO. Frozen autologous non-adherent lymphocytes were thawed, washed once, counted, and $15 \times 10^6$ cells were re-suspended after additional washing in 5 ml of complete medium containing IL-7 (20 ng/ml) and IL-12 (100 pg/ml). 1 ml of lymphocyte suspension was added into wells with dendritic cells. After 7 days, 1 ml of medium was removed, and 1 ml of fresh medium containing IL-7 (20 ng/ml) was added. After 5 days cells were harvested, live cells were separated on Lymphoprep (Nycomed, Norway), and after washing re-suspended in complete medium at $1.5 \times 10^6$/ml. 1 ml of lymphocyte suspension was placed into wells of 24-well plates. Frozen irradiated dendritic cells loaded with lysate were thawed, washed once, resuspended in complete medium at $10^5$/ml, and 1 ml was added into wells with lymphocytes. After 2 days, 1 ml of medium was removed and 1 ml of fresh medium containing IL-2 (20 IU/ml) was added. This procedure of re-stimulation was repeated every week, 2-4 times for each culture.

The lytic activity of lymphocytes was determined after 3-5 rounds of stimulations. At this time, proliferating lymphocytes represent nearly a pure population of CD3-positive cells with an increasing proportion of $CD8^+$ cells after each re-stimulation that reaches 70-90% in one week after 4-$5^{th}$ round of stimulation (phenotype of cells was determined by FACS analysis known in the art using antibody specific against certain surface markers).

In addition to the melanoma cell cultures mentioned above, the following melanoma cell lines were employed: FM28, FM55p, FM60 (HLA-A2-positive), FM45 and FM48 (HLA-A2-negative). These cell lines have been described elsewhere (Bartkova et al, 1996, Cancer Res., v. 56, pp. 5475-5483; Kirkin et al., 1995, Cancer Immunol. Immunother., v. 41, pp. 71-81). The DDB-1 and ANBI-EBV are EBV-transformed lymphoblastoid cell lines established in our laboratory by standard, well known in the art methods. K562 erythroleukemic cells were used as target for NK-mediated lysis. The breast cancer cell lines MCF-7, CAMA-1, HBL-100, MDA-MB-231 (HLA-A2-positive) and BT-20 (HLA-A2-negative) were a kind gift from Dr. Per Briand, Danish Cancer Society. The SCC4 and SCC9 HLA-A2-positive squamous cell carcinoma cell lines were obtained from ATCC. All cell lines were cultured in RPMI 1640 medium supplemented with 10% FCS. Cytotoxic activity was determined as described in Example 1. In experiments with blocking antibodies, the W6/32 monoclonal antibody, specific against common determinant of HLA class I molecules, was added into wells at concentration of 10 μg/ml.

Figure 8:
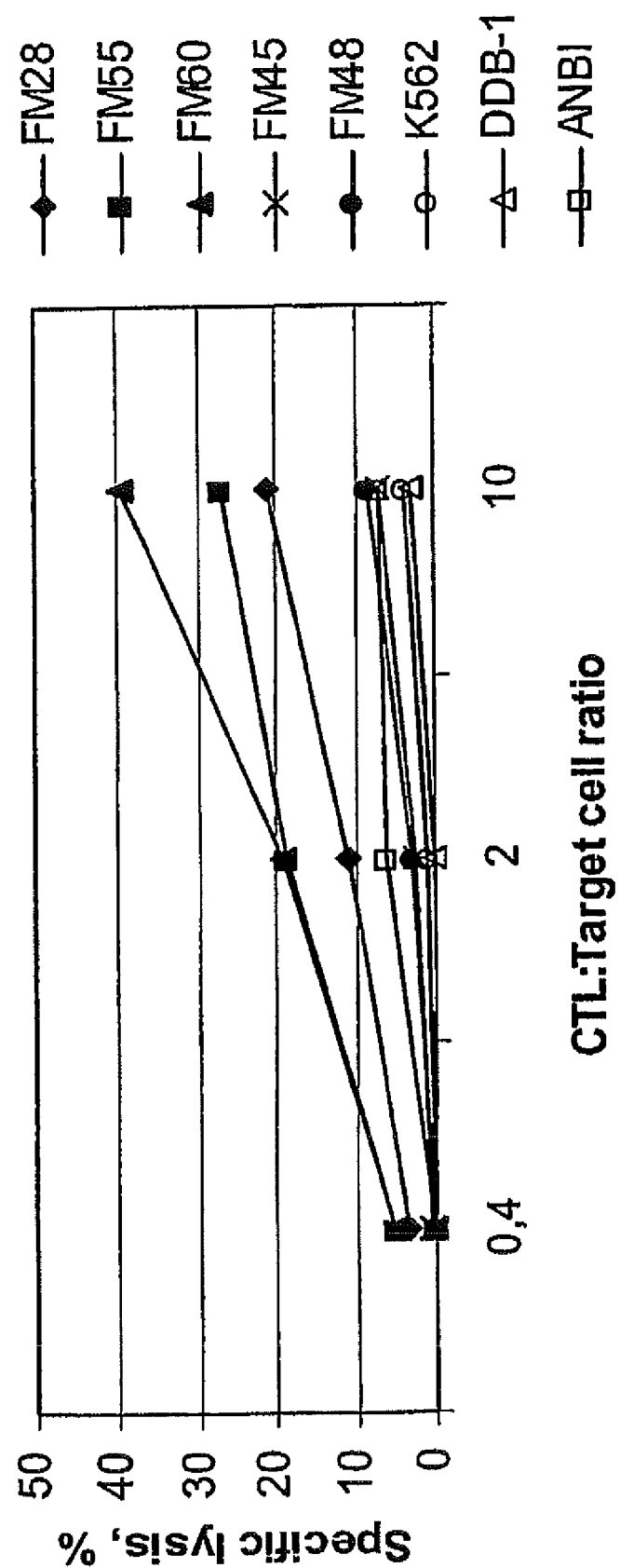
FIG. 8 shows cytolytic activity of immune lymphocytes of donor ANBI against melanoma cells, EBV-transformed B cells and K562 cells.

In the first experiments cytotoxicity was tested against panel of melanoma cells, as well as against EBV-transformed B cells and K562 erythroleukemic cells. NK-like lytic activity, as determined by lysis of K562 cells, was significant after two rounds of stimulations, but was decreased gradually after subsequent stimulations. In order to detect primarily specific CTL-mediated lysis, all experiments on lytic activity were performed in the presence of 20-fold excess of unlabelled K562 cells. The results of the representative experiment on cytotoxicity of lymphocytes from donor ANBI after 4 rounds of stimulations with dendritic cells loaded with lysate of DDM-1.13 cells are shown in FIG. 8. HLA-A2-positive melanoma cells were lysed to different degrees, while K562, ANBI-EBV (EBV-B cells established from the same donor), DDB-1 (autologous to DDM-1 melanoma cells), melanoma cell lines FM45 and FM48 (having no common MHC class I antigens with cells of donor ANBI) were relatively resistant to lysis. It is of note that FM9, HLA-A2-negative melanoma cell line but sharing with donor ANBI HLA-A1 (not shown) is also sensitive to lysis, indicating that HLA restriction of lysis is complex and not restricted by only HLA-A2 antigens. The use of untreated dendritic cells also induced lymphocyte proliferation, albeit at a lower intensity, but development of only nonspecific cytotoxicity was seen in such cultures (not shown). The lack of cytotoxicity against DDB-1 cells, generated from PBMCs (peripheral blood monocytes) of melanoma patient from which DDM-1 melanoma cells have been established, indicates that alloantigens possibly present in the lysate preparation do not induce a significant immune response, and that the resulting immune response is mainly tumor-specific. The W6/32 antibody against MHC class I molecule significantly inhibited, indicating the MHC class I-restricted nature of cytotoxicity. Similar results were obtained with lysate isolated from the DDM-1.7 melanoma clone (not shown).

Figure 9:
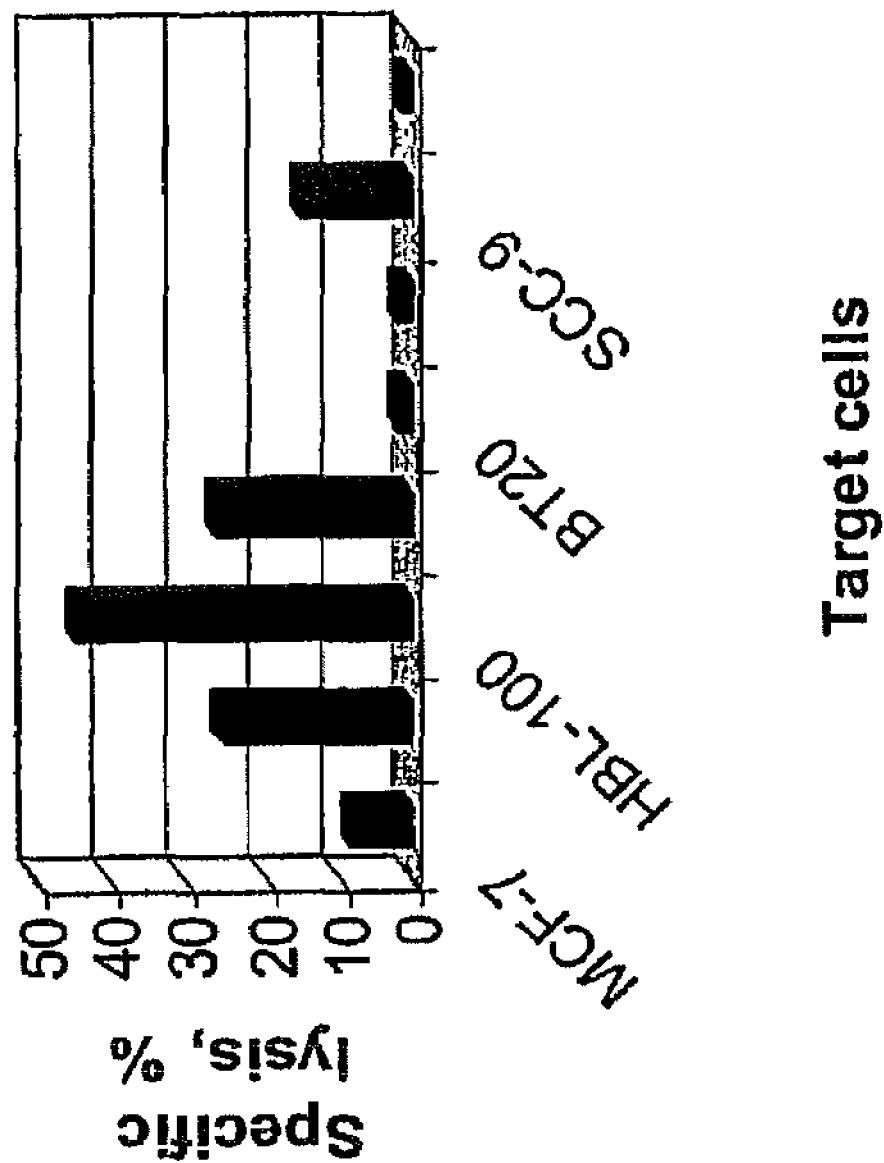
FIG. 9 shows cytolytic activity of immune lymphocytes of donor 19/00 against breast and squamous cell carcinoma cell lines.

To test possibility that recognized antigens belong to a group of cancer/testis antigens, shared between different types of human malignancies, we investigated sensitivity of a number of breast and squamous cell carcinoma lines to lysis by generated CTLs. Results of one experiment are shown in FIG. 9. Three of four HLA-A2-positive breast cancer lines have moderate to high sensitivity to lysis, while one HLA-A2-negative line was completely resistant to lysis. One of two investigated squamous cell carcinoma cell lines was also sensitive to lysis. Lysis of breast cancer cell lines was sensitive to inhibition by HLA class I-specific antibody W6/32. These data demonstrate that in vitro immunization of PBLs (peripheral blood lymphocytes) of a normal donor with autologous dendritic cells loaded with lysate of DDM-1.7 or DDM-1.13 melanoma cell lines induced generation of CTLs that specifically recognized tumor-associated antigens present in several types of human tumors.

Figure 10:
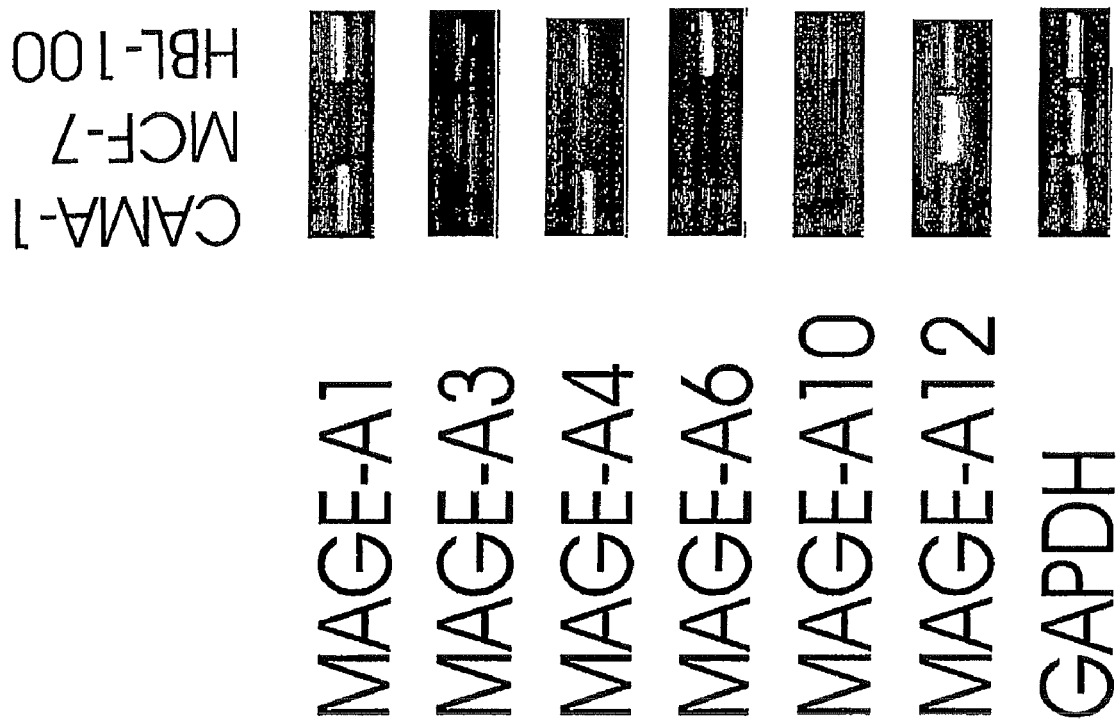
FIG. 10 shows expression of MAGE-A, and GAPDH genes in breast cancer cell lines analyzed by RT-PCR analysis.

One possible group of antigens that could be recognized by CTLs generated in this way is MAGE-A antigens. To correlate the expression of these antigens with the sensitivity of target cells to generated CTLs, we compared levels of expressions of these antigens in three breast cancer lines that show different sensitivity to lysis. Results are presented in FIG. 10. Maximal number of investigated antigens is expressed in HBL-100 cells, while minimal number in MCF-7 cells. These results demonstrate that there is indeed a correlation between number of the expressed genes of MAGE-A groups and sensitivity to lysis, pointing to possibility that these or similarly regulated antigens are major targets upon this type of immunization.

Example 4

Test for Immunodominance of Differentiation Antigens

Two melanoma cell lines expressing high levels of differentiation antigens, DDM-1.29, and low levels of differentiation antigens, DDM-1.P (variant of DDM-1 cell line) were employed in the experiments on the generation of cytotoxic T lymphocytes by in vitro stimulation of peripheral blood lymphocytes with autologous tumor cells according to method described by Hérin et al., 1987, Int. J. Cancer, v. 39, pp. 390-396. After 3 rounds of weekly stimulations of lymphocytes with irradiated tumor cells (10,000 Rad), cell cultures were cloned by limiting dilutions, and lytic activity of growing clones was first tested against original melanoma cell line in a $Cr^{51}$-release test. Cell clones were considered cytotoxic if they had more then 20% lytic activity against original melanoma cell line. The specificity of the cytotoxic T cell clones was then tested in the experiments with T2 cells loaded with different HLA-A2-restricted peptides from the antigens gp100 and MART-1. T2 cells untreated with peptides served as control. Around 100 clones were analyzed for each melanoma cell line. Lysates were loaded on dendritic cells as previously described and autologous lymphocytes were immunized. The proportion of CTL-clones recognizing differentiation antigens gp100 and MART-1 upon immunization was calculated and the results are shown in table 3 below.

TABLE 3

Proportion (% of the total number of generated clones) of the CTL clones recognizing differentiation antigens.

| Melanoma cell line | Expression of differentiation antigens | Proportion (% of the total number of generated clones) of CTL clones recognizing | |
|---|---|---|---|
| | | Gp100 | MART-1 |
| DDM-1.29 | High | 51 | 44 |
| DDM-1.P | Low (less then 5% of levels in DDM-1.29) | 0 | 0 |

The data shows that differentiation antigens are immunodominant. In case of high levels of expression of differentiation antigens, the immune response is directed mainly towards the differentiation antigens gp100 and MART-1, while no induction of immune response is seen when a cell line expressing low levels of differentiation antigens is used for immunization. It should be noted that both cell lines induce intensive proliferation of autologous lymphocytes with generation of large numbers of cytotoxic T cell clones.

Example 5

Phenotype of Dendritic Cells Generated at Different Culture Conditions

In order to investigate how different regimes of lymphokine addition combined with medium change at day 1, would influence the phenotypic properties of the generated immature dendritic cells, four different growth conditions were investigated. Dendritic cells were generated essentially as described in the example 2. The different conditions were:
1) cytokines (GM-CSF and IL-4) were added at day 0 immediately after termination of the adsorption step, and an additional supply of cytokines was added at day 1 without medium change;
2) like group 1, but with a complete medium change at day 1 with additional supply of cytokines;
3) addition of cytokines was delayed until day 1 without medium change at day 1; and
4) the same as group 3, but with a complete medium change at day 1.

The conditions in group 4 correspond to the conditions described by Thurner et al. (1999) for the generation of mature dendritic cells from a leukapheresis product (according to Thurner their optimisation should work only for dendritic cells generated from leukapheresis products, but not from freshly drawn blood samples).

After 5 days of incubation, cells were harvested and the number of large cells was counted on a Coulter Counter (Beckman, model Z2), and the cells were frozen in autologous plasma with the addition of 10% DMSO for further analysis of the expression of surface marker by FACS. The following monoclonal antibodies were used (all from BD Biosciences): CD1a-PE, CD14-FITC, and CD83-PE, with matching control antibodies.

Cell counts demonstrate no difference in the cell yield (in number and size), which is in good correspondence to the data of Thurner et al., 1999, (J. Immunol. Methods 223: 1-15) since they only used morphological criteria and the yield as indicators of growth optimisation. In contrast, significant difference was seen in the present study, when surface markers were measured (results of one of the experiments are presented in Table 4).

TABLE 4

Phenotype of dendritic cells generated
at different culture conditions

| Start of cytokine addition | Medium change at day 1 | DC phenotype (%) | | |
|---|---|---|---|---|
| | | CD1a | CD14 | CD83 |
| Day 0 | No | 20.6 | 12.9 | 26.1 |
| Day 0 | Yes | 18.3 | 9.0 | 34.2 |
| Day 1 | No | 51.0 | 15.4 | 24.9 |
| Day 1 | Yes | 52.0 | 10.9 | 32.8 |

The start of cytokine addition from day 1 significantly up-regulates the expression of the CD1a marker, while not significantly influencing the expression of the other markers. It could also be seen, that medium change at day 1, as originally proposed by Thurner et al (1999), is in fact not necessary, as the same effect was achieved both with and without medium change. A medium change at day 1 in fact significantly decreased endocytic activity of the dendritic cells at the immature state. These conditions—delayed addition of cytokines for 1 day without any medium change were selected for further experiments.

Example 6

Optimization of Yield of Dendritic Cells Producible from Monocytes

During the optimization described above we surprisingly discovered that the yield of dendritic cells obtainable from the mononuclear cell population is dependent on the density of monocytes during the adsorption step. As noted earlier in the majority of published methods, the concentration of mononuclear cells rather than of monocytes is taken into consideration when the adsorption step is performed. However, mononuclear cells represent a mixture of two populations, lymphocytes and monocytes, and the proportion of each population can vary significantly. It is monocytes that predominantly adsorb to the plastic.

To estimate the concentration of monocytes in the population of mononuclear cells we used a Coulter Counter for counting cell number, since this also permits observation of cell size distributions (Beckman, Model Z2). Two major populations of cells, with average sizes of 7 nm (lymphocytes) and 9 nm (monocytes) are seen upon counting, and appropriate gating permits the estimation of the proportion of these two populations.

We have previously found that at a seeding cell density of approximately $15 \times 10^6$ monocytes per T25 flask, adsorption of monocytes was almost complete (more than 90%), and therefore this cell density with variations between $12 \times 10^6$ and $20 \times 10^6$ was used in our experiments. Significant variation in the yields of dendritic cells was observed, and in an attempt to understand the reason for such variation, we decided to relate the yield of dendritic cells in different experiments to the original density of monocytes. Results of such analysis on five cultures generated from different donors clearly indicate the inverse correlation between the efficiency of dendritic cell generation and the density of seeded monocytes.

An experiment was designed to evaluate this relationship, seeding monocytes of the same donor at different densities. Mononuclear cells were isolated from buffy coat (prepared from the blood of healthy donor) by centrifugation on a Lymphoprep gradient. After isolation of interface cells and intensive washing in order to remove platelets, mononuclear cells were suspended in the culture medium consisting of RPMI 1640 medium with addition of 1% of autologous heparinized plasma, and seeded in T25 flasks (surface area of 25 cm$^2$) in 7 ml medium per flask at different amounts of mononuclear cells per flask (from $10 \times 10^6$ to $20 \times 10^6$ of monocytes per flask). After 1 hour adsorption, non-adsorbed cells were removed by washing twice with pre-warmed culture medium, and 7 ml of fresh medium were added into each flask. The next day, GM-CSF (100 ng/ml) and IL-4 (50 µg/ml) were added to the culture. Cytokine addition was repeated at day 3. At day 5, half of medium was changed, and a new portion of GM-CSF and IL-4 was added. At day 6, TNF-α was added at a concentration of 20 ng/ml. The cultures were harvested at day 7, and after counting total number of cells they were frozen, in autologous serum with 10% of DMSO and kept until analyzed by FACS analysis. FACS analysis was performed with CD1a and CD14 antibodies.

The results of one of the experiments regarding the yield of dendritic cells (large cells with the median size between 14 and 16 nm) are presented in the Table 5.

TABLE 5

Yield and phenotype of dendritic cells in cultures
with different initial density of the monocytes

| No. of monocytes per T25 flask ($\times 10^6$) | No. of DC's per T25 flask ($\times 10^6$) | Yield of DC's, % of monocytes | DC phenotype, % of gated cells | |
|---|---|---|---|---|
| | | | CD1a | CD14 |
| 10 | 5.28 | 52.8 | 54.9 | 11.0 |
| 12.5 | 5.43 | 43.4 | 44.9 | 16.9 |
| 15 | 4.67 | 31.1 | 46.4 | 14.9 |
| 17.5 | 4.47 | 25.5 | 46.2 | 14.5 |
| 20 | 4.69 | 23.4 | 44.2 | 7.4 |

The yield of dendritic cells was significantly decreased with increasing density of the seeded monocytes, being 50% at minimal cell density. The results of a FACS analysis performed on the same dendritic cells are also presented in the table and indicate that no significant difference was observed in the properties of dendritic cells generated under initially different density of the monocytes.

Decreasing the initial cell density of monocytes below $10 \times 10^6$ cells per T25 flask leads to a decrease in the expression of the CD1a marker (data not shown). Therefore, the optimal cell density of initial monocyte population leading to the maximal efficiency of the production of dendritic cells with maximal competence (as judged by the expression of the major DC markers) is around $10 \times 10^6$ cells per 25 cm2 of culture surface.

Based on these data, it is now possible to calculate the volume of blood that will be necessary to draw. If the expected yield of dendritic cells is about 50% of the initial number of monocytes, then it will require only 300 ml of blood to obtain $50 \times 10^6$ dendritic cells. This means, that one single blood sample of 300 ml of blood should be enough for the preparation of a vaccine for two rounds of vaccinations. The required amount of cytokines (21 ng for GM-CSF and 10.5 ng for IL-4), as well as other materials is three times lower than in the standard, non-optimized method. Therefore, also the cost of materials needed for the DC production will be at least three times lower, and in addition there will be no need for conducting expensive leukapheresis procedures.

Example 7

Use of Dendritic Cell Based Vaccine

A vaccination cycle of cancer patients with dendritic cells loaded with the lysate of two melanoma cell lines prepared according to the invention, should preferably be designed in such a way that patients will receive a first cycle of five intradermal vaccinations with 3 week intervals, each time with $5 \times 10^6$ dendritic cells. If a clinical response is seen after the initial cycle of vaccinations, a second, similar cycle will be conducted. For the whole period of the trial a total of up to $50 \times 10^6$ cells will be required. Considering the condition of the patients (the majority of patients are at advanced stages of disease, where no other treatments are working anymore), it is important to minimize the numbers of blood drawings, restricting them to one or two.

The invention claimed is:

1. A melanoma cell line DDM-1.7 deposited as ECACC 01112339.

2. A melanoma cell line DDM-1.13 deposited as ECACC 01112338.

3. Exosomes obtained from a cell line DDM-1.7 (ECACC 01112339) or DDM-1.13 (ECACC 01112338).

* * * * *

SEQUENCE LISTING

```
<160> NUMBER OF SEQ ID NOS: 20

<210> SEQ ID NO 1
<211> LENGTH: 18
<212> TYPE: DNA
<213> ORGANISM: Homo sapiens
<220> FEATURE:
<221> NAME/KEY: misc_feature
<223> OTHER INFORMATION: GADPH sense primer

<400> SEQUENCE: 1
aggggggagc caaaaggg                                                       18

<210> SEQ ID NO 2
<211> LENGTH: 19
<212> TYPE: DNA
<213> ORGANISM: Homo sapiens
<220> FEATURE:
<221> NAME/KEY: misc_feature
<223> OTHER INFORMATION: GADPH anti-sense primer

<400> SEQUENCE: 2
gaggagtggg tgtcgctgt                                                      19

<210> SEQ ID NO 3
<211> LENGTH: 21
<212> TYPE: DNA
<213> ORGANISM: Homo sapiens
<220> FEATURE:
<221> NAME/KEY: misc_feature
<223> OTHER INFORMATION: Gp100 sense primer

<400> SEQUENCE: 3
ggctggtgaa gagacaagtc c                                                   21

<210> SEQ ID NO 4
<211> LENGTH: 21
<212> TYPE: DNA
<213> ORGANISM: Homo sapiens
<220> FEATURE:
<221> NAME/KEY: misc_feature
<223> OTHER INFORMATION: Gp100 anti-sense primer

<400> SEQUENCE: 4
agagatgcaa ggaccacagc c                                                   21

<210> SEQ ID NO 5
<211> LENGTH: 23
<212> TYPE: DNA
<213> ORGANISM: Homo sapiens
<220> FEATURE:
<221> NAME/KEY: misc_feature
<223> OTHER INFORMATION: Mart-1 sense primer
```

<400> SEQUENCE: 5
gaaggtgtcc tgtgccctga ccc                                              23

<210> SEQ ID NO 6
<211> LENGTH: 26
<212> TYPE: DNA
<213> ORGANISM: Homo sapiens
<220> FEATURE:
<221> NAME/KEY: misc_feature
<223> OTHER INFORMATION: Mart-1 anti-sense primer

<400> SEQUENCE: 6
ggcttgcatt tttcctacac cattcc                                           26

<210> SEQ ID NO 7
<211> LENGTH: 19
<212> TYPE: DNA
<213> ORGANISM: Homo sapiens
<220> FEATURE:
<221> NAME/KEY: misc_feature
<223> OTHER INFORMATION: MAGE-A1 sense primer

<400> SEQUENCE: 7
gattccctgg aggccacag                                                   19

<210> SEQ ID NO 8
<211> LENGTH: 21
<212> TYPE: DNA
<213> ORGANISM: Homo sapiens
<220> FEATURE:
<221> NAME/KEY: misc_feature
<223> OTHER INFORMATION: MAGE-A1 anti-sense primer

<400> SEQUENCE: 8
cctcactggg ttgcctctgt c                                                21

<210> SEQ ID NO 9
<211> LENGTH: 20
<212> TYPE: DNA
<213> ORGANISM: Homo sapiens
<220> FEATURE:
<221> NAME/KEY: misc_feature
<223> OTHER INFORMATION: MAGE-A3 sense primer

<400> SEQUENCE: 9
accagaggcc cccggaggag                                                  20

<210> SEQ ID NO 10
<211> LENGTH: 23
<212> TYPE: DNA
<213> ORGANISM: Homo sapiens
<220> FEATURE:
<221> NAME/KEY: misc_feature
<223> OTHER INFORMATION: MAGE-A3 anti-sense primer

<400> SEQUENCE: 10
ctgccaattt ccgacgacac tcc                                              23

<210> SEQ ID NO 11
<211> LENGTH: 18
<212> TYPE: DNA
<213> ORGANISM: Homo sapiens
<220> FEATURE:
<221> NAME/KEY: misc_feature
<223> OTHER INFORMATION: MAGE-A4 sense primer

<400> SEQUENCE: 11
gagcagacag gccaaccg                                                18

<210> SEQ ID NO 12
<211> LENGTH: 18
<212> TYPE: DNA
<213> ORGANISM: Homo sapiens
<220> FEATURE:
<221> NAME/KEY: misc_feature
<223> OTHER INFORMATION: MAGE-A4 anti-sense primer

<400> SEQUENCE: 12
aaggactctg cgtcaggc                                                18

<210> SEQ ID NO 13
<211> LENGTH: 16
<212> TYPE: DNA
<213> ORGANISM: Homo sapiens
<220> FEATURE:
<221> NAME/KEY: misc_feature
<223> OTHER INFORMATION: MAGE-A6 sense primer

<400> SEQUENCE: 13
aggaccagag gccccc                                                  16

<210> SEQ ID NO 14
<211> LENGTH: 22
<212> TYPE: DNA
<213> ORGANISM: Homo sapiens
<220> FEATURE:
<221> NAME/KEY: misc_feature
<223> OTHER INFORMATION: MAGE-A6 anti-sense primer

<400> SEQUENCE: 14
ggatgattat caggaagcct gt                                           22

<210> SEQ ID NO 15
<211> LENGTH: 21
<212> TYPE: DNA
<213> ORGANISM: Homo sapiens
<220> FEATURE:
<221> NAME/KEY: misc_feature
<223> OTHER INFORMATION: MAGE-A10 sense primer

<400> SEQUENCE: 15
cacagagcag cactgaagga g                                            21

<210> SEQ ID NO 16
<211> LENGTH: 23
<212> TYPE: DNA
<213> ORGANISM: Homo sapiens
<220> FEATURE:
<221> NAME/KEY: misc_feature
<223> OTHER INFORMATION: MAGE-A10 anti-sense primer

<400> SEQUENCE: 16
ctgggtaaag actcactgtc tgg                                          23

<210> SEQ ID NO 17
<211> LENGTH: 18
<212> TYPE: DNA
<213> ORGANISM: Homo sapiens
<220> FEATURE:
<221> NAME/KEY: misc_feature
<223> OTHER INFORMATION: MAGE-A12 sense primer

<400> SEQUENCE: 17

```
<210> SEQ ID NO 18
<211> LENGTH: 22
<212> TYPE: DNA
<213> ORGANISM: Homo sapiens
<220> FEATURE:
<221> NAME/KEY: misc_feature
<223> OTHER INFORMATION: MAGE-A12 anti-sense primer

<400> SEQUENCE: 18
gccctccact gatctttagc aa                                       22

<210> SEQ ID NO 19
<211> LENGTH: 14
<212> TYPE: DNA
<213> ORGANISM: Homo sapiens
<220> FEATURE:
<221> NAME/KEY: misc_feature
<223> OTHER INFORMATION: NY-ESO-1 sense primer

<400> SEQUENCE: 19
ggcacagggg gttc                                                14

<210> SEQ ID NO 20
<211> LENGTH: 19
<212> TYPE: DNA
<213> ORGANISM: Homo sapiens
<220> FEATURE:
<221> NAME/KEY: misc_feature
<223> OTHER INFORMATION: NY-ESO-1 anti-sense primer

<400> SEQUENCE: 20
gcttagcggc ctctgccct                                           19
```
tggaagtggt ccgcatcg    18